(12) United States Patent
Bulla, Jr. et al.

(10) Patent No.: US 8,241,844 B2
(45) Date of Patent: Aug. 14, 2012

(54) METHODS AND COMPOSITIONS FOR MODULATING AN IMMUNE RESPONSE WITH IMMUNOGENIC OLIGONUCLEOTIDES

(76) Inventors: Lee A. Bulla, Jr., Tioga, TX (US); Jeffrey Marcus Clark, Lancaster, TX (US); Ralph Clark, legal representative, Lancaster, TX (US); Natalya Griko, Lewisville, TX (US); Jian Sun, Irving, TX (US)

(*) Notice: Subject to any disclaimer, the term of this patent is extended or adjusted under 35 U.S.C. 154(b) by 0 days.

(21) Appl. No.: 12/572,494

(22) Filed: Oct. 2, 2009

(65) Prior Publication Data

US 2010/0119556 A1 May 13, 2010

Related U.S. Application Data

(60) Provisional application No. 61/234,431, filed on Aug. 17, 2009, provisional application No. 61/102,641, filed on Oct. 3, 2008.

(51) Int. Cl.
  *C12Q 1/70* (2006.01)
  *C12Q 1/68* (2006.01)
  *A61K 39/12* (2006.01)
  *C07H 21/02* (2006.01)
(52) U.S. Cl. .......... 435/5; 435/6.1; 424/204.1; 536/23.1
(58) Field of Classification Search ........................ None
  See application file for complete search history.

(56) References Cited

U.S. PATENT DOCUMENTS

| | | | |
|---|---|---|---|
| 4,469,863 A | 9/1984 | Ts'o et al. |
| 5,033,252 A | 7/1991 | Carter |
| 5,052,558 A | 10/1991 | Carter |
| 5,323,907 A | 6/1994 | Kalvelage |
| 7,105,495 B2 | 9/2006 | Agrawal et al. |
| 7,176,296 B2 | 2/2007 | Agrawal et al. |

OTHER PUBLICATIONS

Krieg et al Journal of Immunology 1989 vol. 143 No. 8 pp. 2448-2451.*
Henault et al. Journal Immunological Methods (2005) pp. 93-99.*
Authorized Officer, Athina Nickitas-Etienne, International Preliminary Report on Patentability, International Application No. PCT/US2009/059347, mailed Apr. 14, 2011, 7 pages.
Korber et al., "Numbering Positions in HIV Relative to HXB2CG," available at hiv.lanl.gov/content/sequence/HIV/REVIEWS/HXB2.html on the World Wide Web.
Agrawal et al., "Pharmacokinetics, biodistribution, and stability of oligodeoxynucleotide phosphorothioates in mice," *Proc. Nat'l Acad. Sci. USA*, 1991, 88:7595-7599.
Ansel, *Introduction to Pharmaceutical Dose Forms*, Fourth Edition 1985, 126.
Asagiri et al., "Cathepsin K-Dependent Toll-Like Receptor 9 Signaling Revealed in Experimental Arthritis," *Science*, Feb. 1, 2008, vol. 319, pp. 624-627.
Beaucage et al., "Deoxynucleotide phosphoramidites—A new class of key intermediates for deoxypolynucleotide synthesis," *Tet. Let.*, 1981, 22:1859-1862.
Fabrick et al., "Innate Immunity in a Pyralid Moth functional evaluation of domains from a β-1,3-glucan recognition protein," *J. Biol. Chem.*, 2004, 279:26605-26611.
Froehler et al., "Synthesis of DNA via deoxynudeoside H-phosphonate Intermediates," *Nucl. Acid Res.*, 1986, 14:5399-5407.
Gaffney et al., "Large-scale oligonucleotide synthesis by the H-phosphonate method," *Tet. Let.*, 1988, 29:2619-2622.
Garegg et al., "Nucleoside H-phosphonates III. Chemical synthesis of oligodeoxyribonucleotides by the hydrogenphosphonate approach," *Tet. Let.*, 1986, 27:4051-4054.
Garegg et al., "Nucleoside H-phosphonates. IV. Automated solid phase synthesis of oligoribonucleotides by the hydrogenphosphonate approach," *Tet. Let.*, 1986, 27: 4055-4058.
GenBank Accession No. K03455, dated Oct. 21, 2002, 6 pages.
Goodchild, "Conjugates of oligonucleotides and modified oligonucleotides: a review of their synthesis and properties," *Bioconjugate Chem.*, 1990, 1(3):165-187.
Hornung et al., "Quantitative Expression of Toll-Like Receptor 1-10 mRNA in Cellular Subsets of Human Peripheral Blood Mononuclear Cells and Sensitivity to CpG Oligodeoxynucleotides," Journal of Immunology, 2002, vol. 168, pp. 4531-4537.
Korber et al., "Numbering Positions in HIV Relative to HXB2CG," available at hiv.lanl.gov/content/sequence/HIV/REVIEWS/HXB2.html on the World Wide Web, 1998.
Luganini et al., "Phosphorothioate-Modified Oligodeoxynucleotides Inhibit Human Cytomegalovirus Replication by Blocking Virus Entry," *Antimicrob Agents Chemother.*, 2008, 52(3):1111-1120.
Stein et al., "Physicochemical properties of phospborothioate oligodeoxynucleotides," *Nucleic Acids Res.*, 1988, 16:3209-3221.
Takeshita et al., "Cutting Edge: Role of Toll-Like Receptor 9 in CpG DNA-Induced Activation of Human Cells," *Journal of Immunology*, 2001, vol. 167, pp. 3555-3558.
Tosi, "Innate immune responses to infection," *J. Allergy Clin. Immunol.*, 2005, 116:241-249.
Uhlmann and Peyman, "Antisense oligonucleotides: a new therapeutic principle," *Chem. Rev.*, 1990, 90:543-584.
Wagner, "Interactions between bacterial CpG-DNA and TLR9 bridge innate and adaptive immunity," *Current Opinion in Microbiology*, 2002, vol. 5, pp. 62-69.
Authorized Officer, Kim, Jung Tae, Korean Intellectual Property Office, PCT/US2009/059347, International Search Report & Written Opinion Apr. 23, 2010, 14 pages.
Korber et al., Numbering Positions in HIV Relative to HXB2CG, in the database compendium, Human Retroviruses and AIDS, 1998.

* cited by examiner

*Primary Examiner* — Nita M Minnifield
*Assistant Examiner* — Nina Archie
(74) *Attorney, Agent, or Firm* — Carstens & Cahoon, LLP; Vincent J. Allen

(57) ABSTRACT

This document relates to compositions and methods for modulating an immune response. For example, compositions of immunostimulatory CpG oligonucleotides derived from retroviral genomes are provided.

9 Claims, 17 Drawing Sheets

FIGURE 7
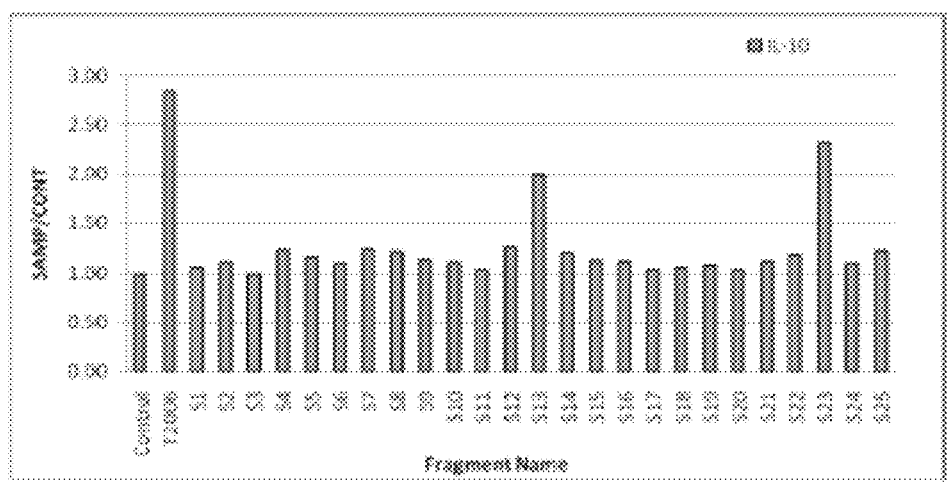
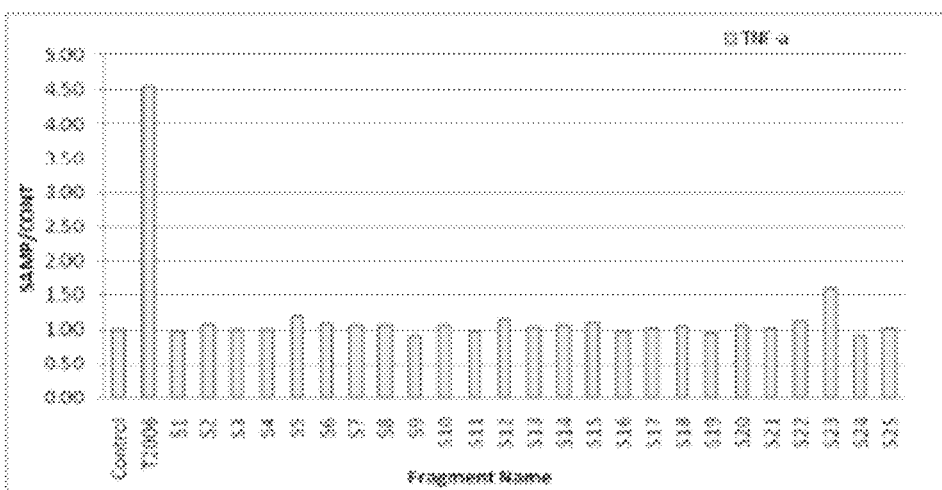
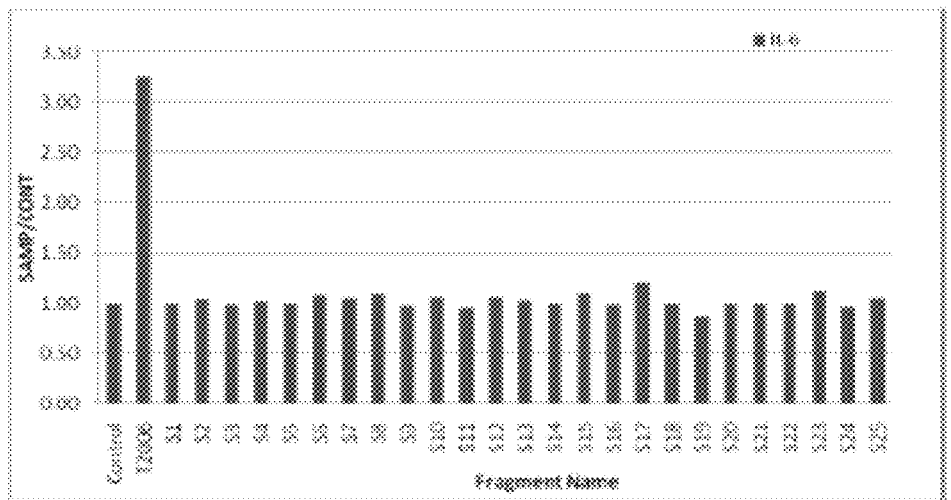

FIGURE 8
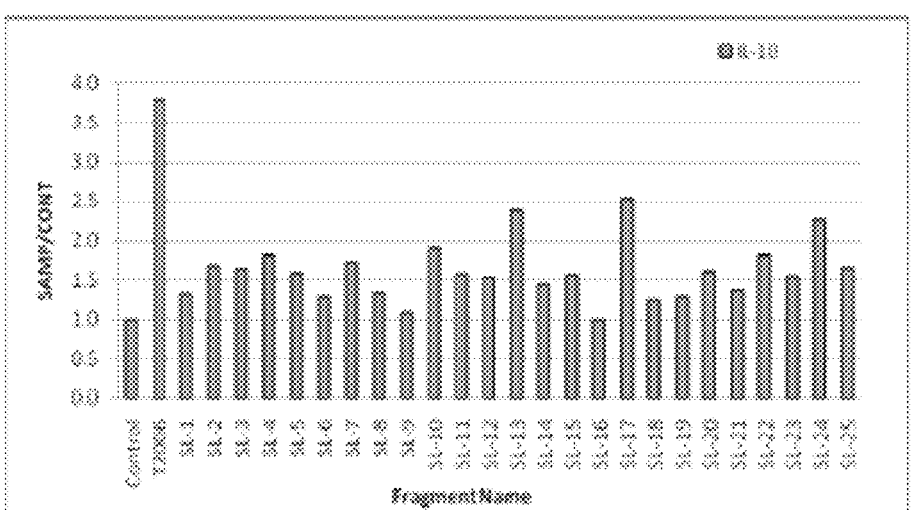
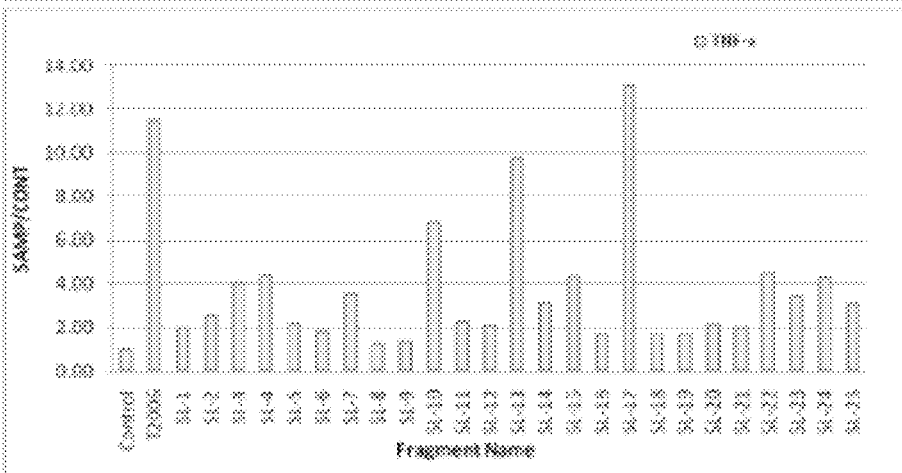
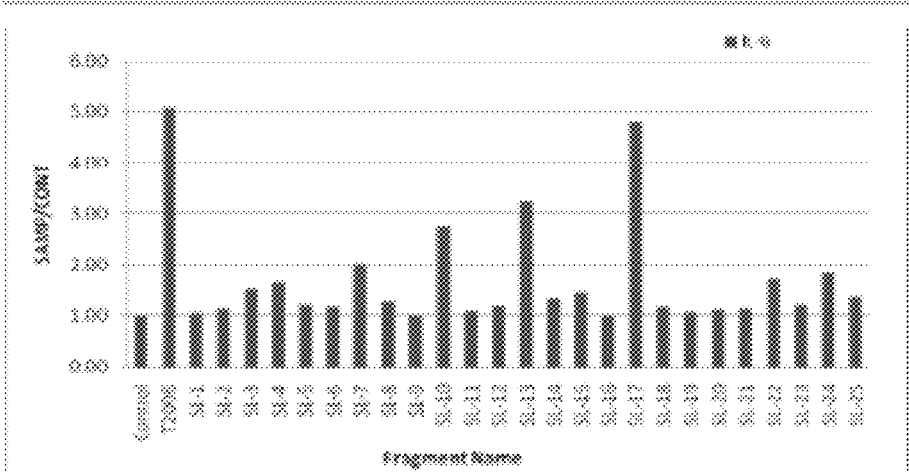

FIGURE 11
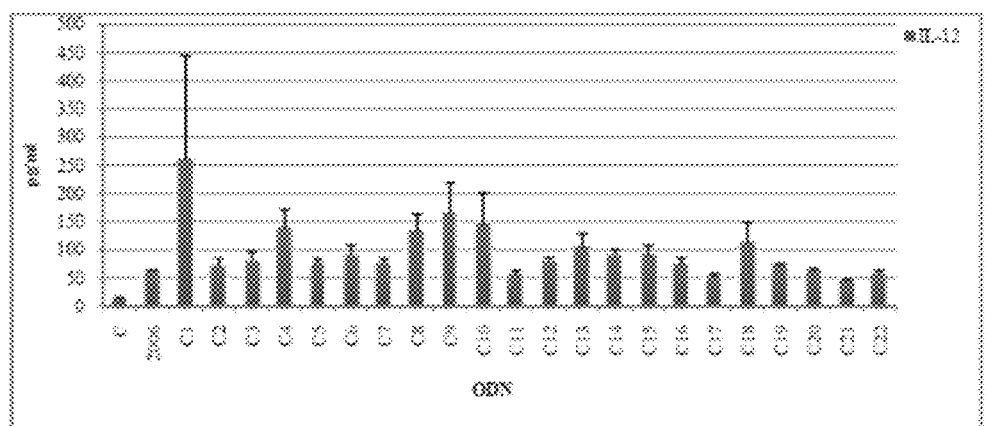
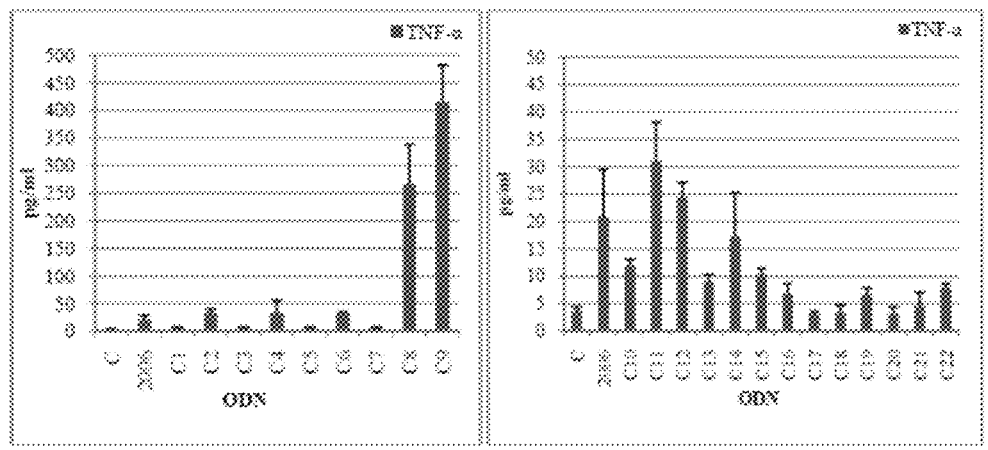
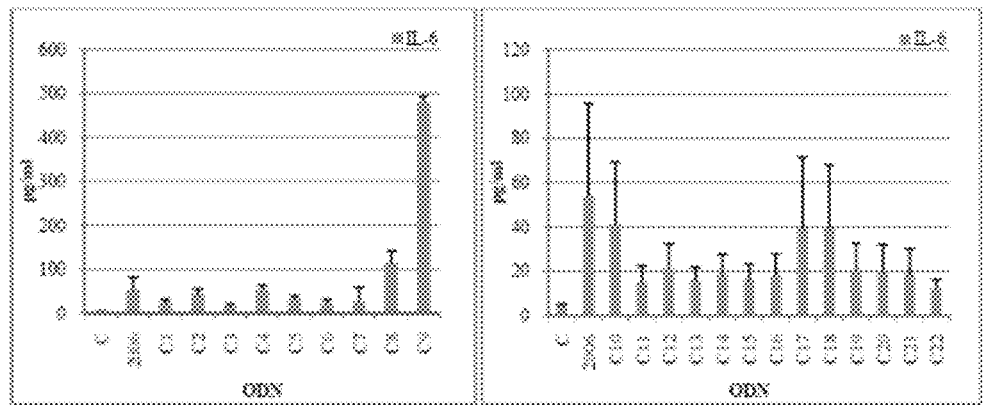

FIGURE 12
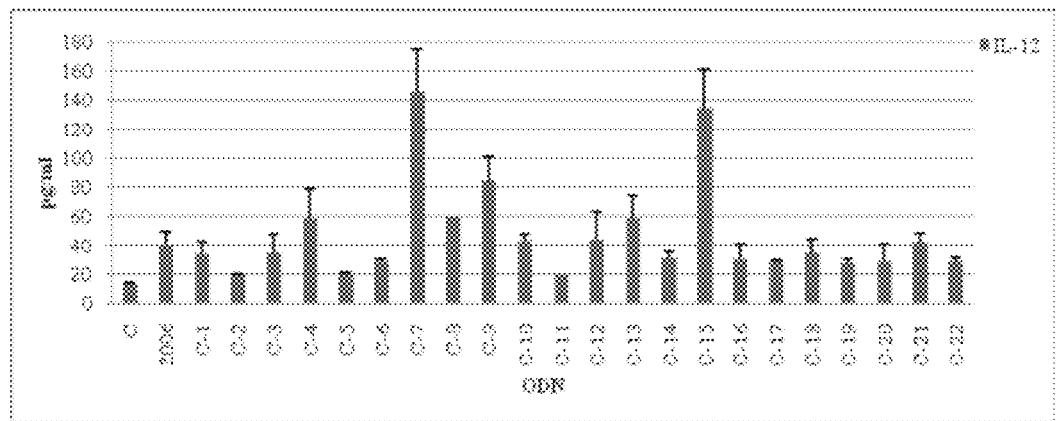
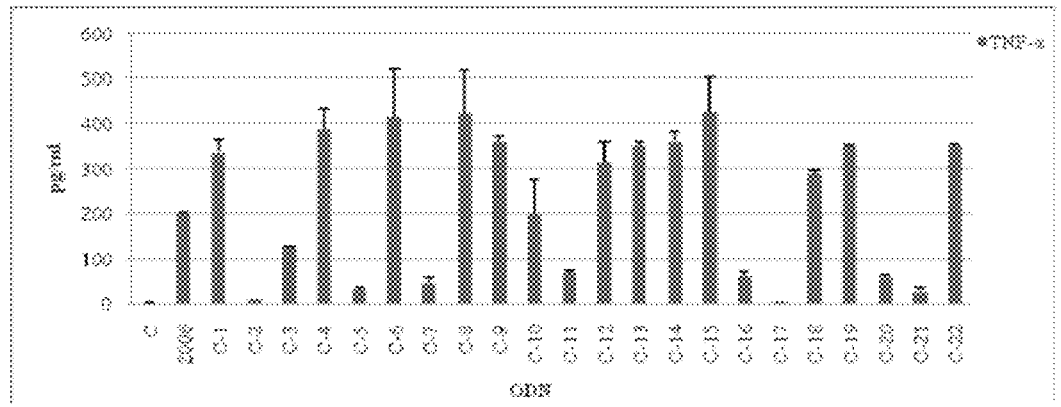
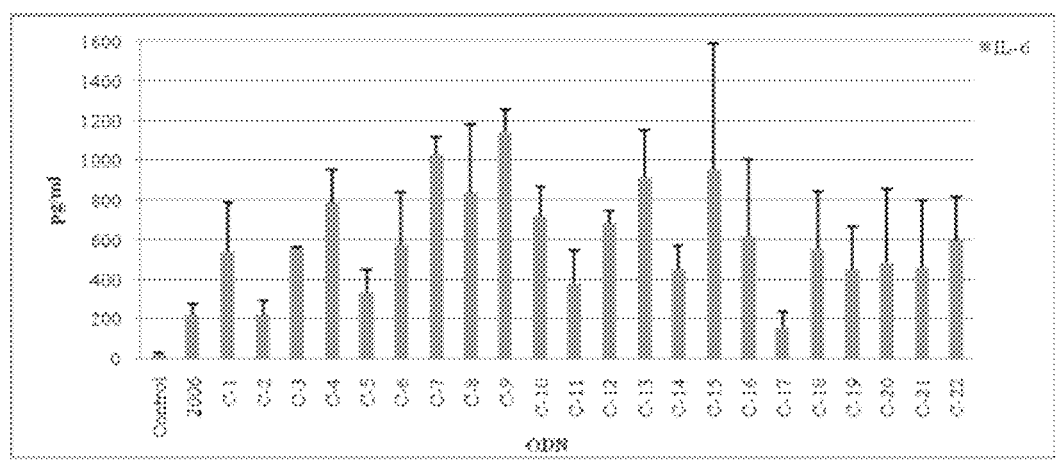

FIGURE 13
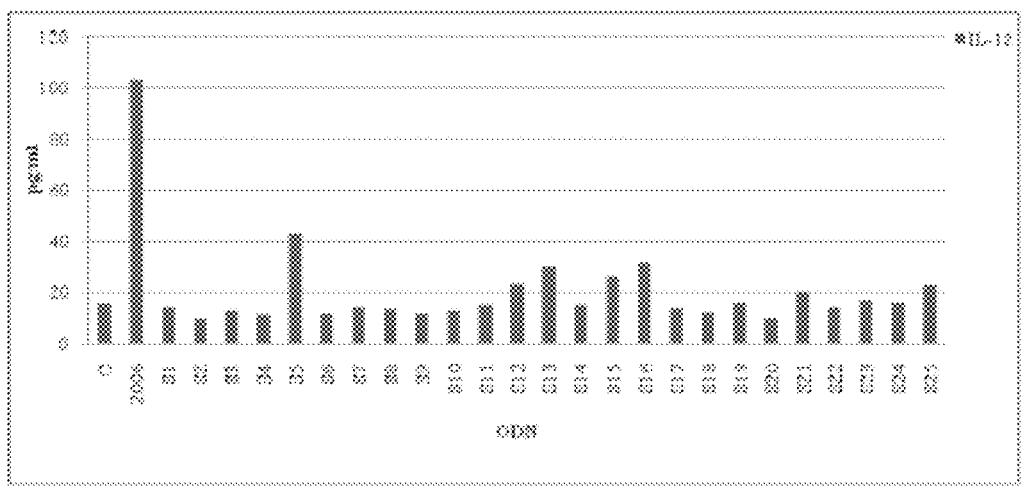
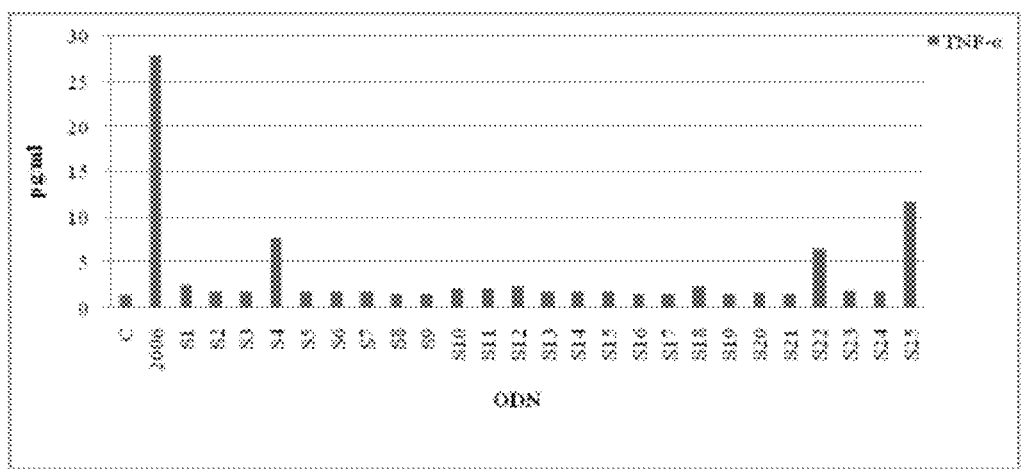
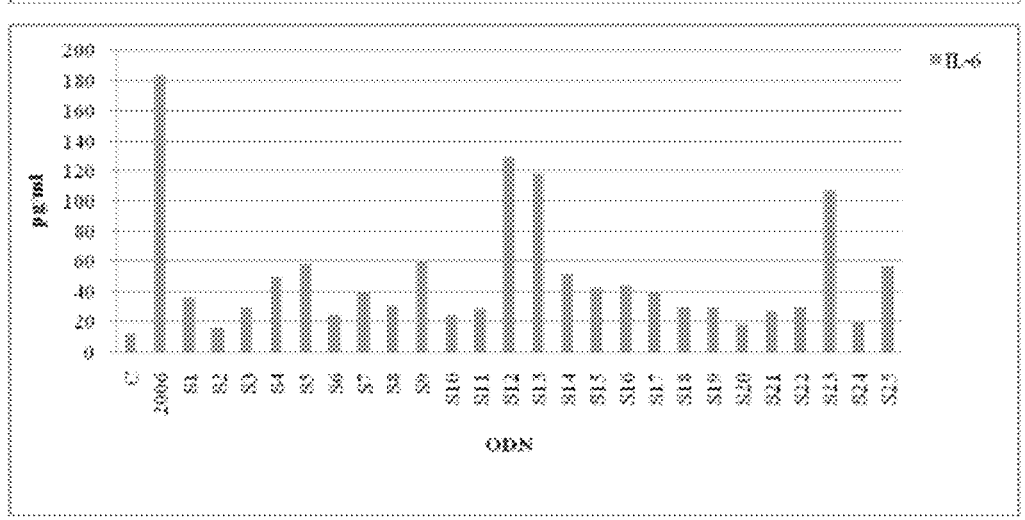

FIGURE 15
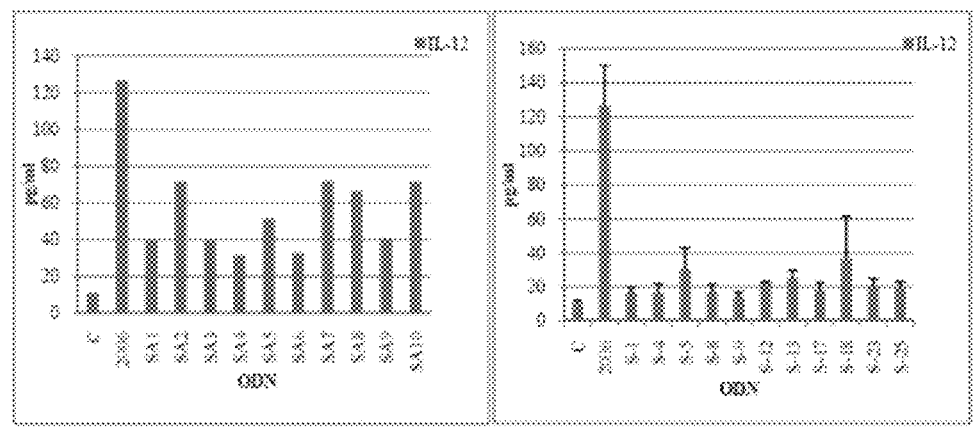
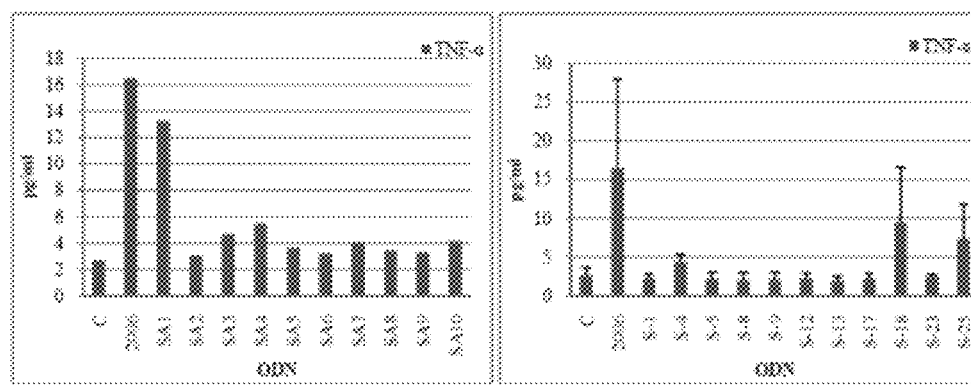
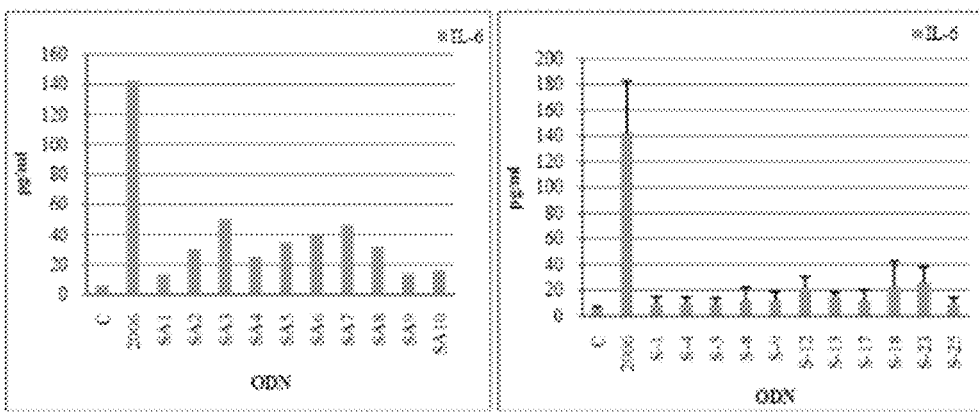

METHODS AND COMPOSITIONS FOR MODULATING AN IMMUNE RESPONSE WITH IMMUNOGENIC OLIGONUCLEOTIDES

CLAIM OF PRIORITY

This application claims priority to U.S. Provisional Application Ser. No. 61/234,431, filed on Aug. 17, 2009, and U.S. Provisional Application Ser. No. 61/102,641, filed on Oct. 3, 2008, which are incorporated by reference in its entirety herein.

TECHNICAL FIELD

This document relates to compositions and methods for modulating an immune response. For example, this document provides compositions of immunostimulatory CpG oligonucleotides derived from retroviral genomes.

BACKGROUND

The cells of the innate immune system, such as dendritic cells (DCs), provide an immune response that does not depend upon specific antigen recognition. See, for example, Tosi, *J. Allergy Clin. Immunol.* 116:241-49 (2005). Dendritic cells lack the highly specific antigen receptors of T and B cells, and rely instead on a set of pattern recognition receptors ("PRRs"), which recognize and bind pathogen-associated molecular patterns and thereby transduce an immune response signal. Fabrick et al., *J. Biol. Chem.* 279:26605-11 (2004). Illustrative of the class of PRRs are the Toll-like receptors ("TLRs"), which recognize a range of molecular patterns and generate intracellular signals for activating a number of host responses. Toll-like receptors such as TLR-9 detect microbial DNA by recognizing the presence of unmethylated cytidine-guanosine (CG) dinucleotides within certain base contexts, or "CpG motifs." The interaction between microbial DNA and TLR-9 receptor induces cell signaling pathways which include mitogen-activated protein kinases and NFκB. These signaling events, in turn, provoke leukocyte gene expression and cytokine secretion. CpG motifs are not prominent in vertebrate genomes due to a phenomenon known as "CpG suppression," but are present at the expected frequency in prokaryotic DNA. This contrast has been attributed to evolution of the vertebrate immune system to recognize unmethylated CpG motifs and respond with a coordinated cytokine response.

SUMMARY

The methods and materials provided herein are based in part on the discovery that ODNs of desired immunogenicity can be designed on the basis of CG motifs endogenous to a viral or retroviral genome such as the Human Immunodeficiency Virus-1 (HIV-1) genome. As described herein, immunogenic oligonucleotides can be isolated nucleic acids containing CpG motifs that have nucleotide sequences derived from the HIV-1 viral genome, the Simian Immunodeficiency Virus (SIV) genome, or another viral or retroviral genome. In some cases, the isolated nucleic acids can have sequences having modifications or substitutions relative to HIV-1, SIV, or other retroviral genomes. As described herein, such immunogenic oligonucleotides can be used to stimulate lymphocytes to produce an immune response as determined by stimulated cytokine production. In some cases, oligonucleotides can be used to modulate the immune response as determined by altered cytokine production. The methods and materials provided herein can allow a clinician or other medical professional to restore immune function in a mammal with an immunodeficiency disorder and/or to treat an infection or other disorder by modulating cytokine production.

In general, this document features an isolated nucleic acid. The isolated nucleic acid can consist of from 20-84 contiguous nucleotides of a mammalian retroviral sequence. The isolated nucleic acid can comprise at least one CpG motif, with the proviso that at least one non-thymidine nucleotide 1, 2, or 3 bases immediately 5' or immediately 3' to the CpG motif is substituted with thymidine. The isolated nucleic acid can be 20-50 nucleotides in length. The isolated nucleic acid can be 24 nucleotides in length. The isolated nucleic acid can comprise a sequence selected from the group consisting of SEQ ID NO:28, 29, 30, 31, 32, 33, 34, 35, 36, 37, 38, 39, 40, 41, 42, 43, 44, 45, 46, 47, 48, 49, 50, 51, 52, 75, 76, 77, 78, 79, 80, 81, 82, 83, and 84. The mammalian retroviral sequence can be a HIV genomic sequence. The mammalian retroviral sequence can be a SIV genomic sequence.

In another aspect, this document features an isolated nucleic acid. The isolated nucleic acid can have a nucleotide sequence consisting of a sequence selected from the group consisting of SEQ ID NO:28, 29, 30, 31, 32, 33, 34, 35, 36, 37, 38, 39, 40, 41, 42, 43, 44, 45, 46, 47, 48, 49, 50, 51, 52, 75, 76, 77, 78, 79, 80, 81, 82, 83, and 84.

In another aspect, this document features an isolated nucleic acid. The isolated nucleic acid can have a nucleotide sequence consisting of SEQ ID NO:26. The isolated nucleic acid of can comprise one or more phosphate backbone modifications. The isolated nucleic acid can comprise one or more nucleotide analogues. The isolated nucleic acid can comprise at least one stabilizing element.

In another aspect, this document features a composition. The composition can comprise the nucleic acid and a therapeutic antigen.

In another aspect, this document features a method for stimulating lymphocyte cytokine production. The method can comprise contacting lymphocytes with the nucleic acid under conditions wherein the cytokine production is enhanced relative to uncontacted lymphocytes. The contacted lymphocytes can form primed lymphocytes. The method can further comprise administering the primed lymphocytes to a mammal. The contacting can be in vivo. The contacting can further comprise application of a therapeutic antigen. The stimulation can be measured according to a TLR-9 antagonism assay. The cytokine can be selected from the group consisting of IL-6, IL-10, IL-12, and TNF-α, or any combination thereof. The administering can comprise intranasal, oral, transdermal, intranasal, parenteral, intraperitoneal, intrathecal, rectal, or vaginal administration.

In another aspect, this document features a method for stimulating lymphocyte cytokine production. The method can comprise contacting lymphocytes with an isolated nucleic acid under conditions wherein said cytokine production is enhanced relative to uncontacted lymphocytes. The isolated nucleic acid can consist of a nucleotide sequence selected from the group consisting of SEQ ID NO:1, 2, 3, 4, 5, 6, 7, 8, 9, 10, 11, 12, 13, 14, 15, 16, 17, 18, 19, 20, 21, 22, 23, 24, 25, 53, 54, 55, 56, 57, 58, 59, 60, 61, 62, 63, 64, 65, 66, 67, 68, 69, 70, 71, 72, 73, and 74. The contacted lymphocytes can form primed lymphocytes. The method can further comprise administering the primed lymphocytes to a mammal. The contacting can be in vivo. The contacting can further comprise application of a therapeutic antigen. The stimulation can be measured according to a TLR-9 antagonism assay.

The cytokine can be selected from the group consisting of IL-6, IL-10, IL-12, and TNF-α, or any combination thereof. The administering can comprise intranasal, oral, transdermal, intranasal, parenteral, intraperitoneal, intrathecal, rectal, or vaginal administration.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 7 is a series of bar graphs, each graph depicting the level of production of IL-10 (A), TNF-α (B), and IL-6 (C), respectively, by Namalwa cells stimulated by one of 25 ODNs having a sequence derived from the HIV genome.

FIG. 8 is a series of bar graphs, each graph depicting the level of production of IL-10 (A), TNF-α (B), and IL-6 (C), respectively, by Namalwa cells stimulated by one of 25 ODNs, each ODN a variant of an ODN presented in FIG. 5.

FIG. 11 presents a series of bar graphs depicting the production of cytokines Interleukin-12 (IL-12) (A), TNF-α (B), and IL-6 (C) in monkey lymphocytes following treatment with SIV-derived ODNs. Data are presented as mean±SEM.

FIG. 12 presents a series of bar graphs depicting the production of cytokines IL-12 (A), TNF-α (B), and IL-6 (C) in human peripheral blood mononuclear cells (PBMCs) following treatment with SIV-derived ODNs. Data are presented as mean±SEM.

FIG. 13 presents a series of bar graphs depicting the production of cytokines IL-12 (A), TNF-α (B), and IL-6 (C) in human PBMCs following treatment with HIV-derived ODNs.

FIG. 15 presents a series of bar graphs depicting the production of cytokines IL-12 (A), TNF-α (B), and IL-6 (C) in monkey lymphocytes following treatment with 2 sets of HIV-derived ODNs. Data are presented as mean±SEM.

DETAILED DESCRIPTION

Figure 1:
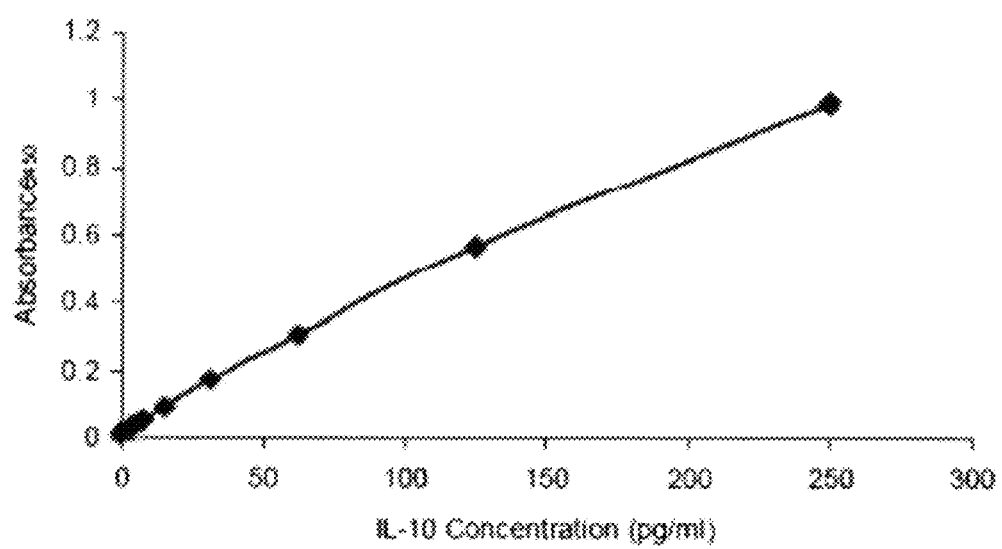
FIG. 1 is a graph exemplifying standard measurement curves (absorbance vs. concentration) for Interleukin-10 (IL-10), with respect to an enzyme-linked immunosorbent assay (ELISA) for monitoring the immuno-responses of Namalwa cells in vitro.

The methods and materials provided herein are based in part on the discovery that oligonucleotides (ODNs) of desired immunogenicity can be designed on the basis of CG motifs endogenous to a retroviral genome such as the Human Immunodeficiency Virus-1 (HIV-1) genome. As described herein, immunogenic ODNs can be isolated nucleic acids containing CpG motifs that have nucleotide sequences derived from a retroviral genome (e.g., the HIV-1 viral genome, the SIV genome). In some cases, the isolated nucleic acids can have sequences having modifications or substitutions relative to HIV-1, SIV, or other mammalian retroviral genomes. As described herein, such immunogenic oligonucleotides can be used to stimulate lymphocytes to produce an immune response as determined by stimulated cytokine production. In some cases, oligonucleotides potentially can be used to suppress an immune response as determined by reduced cytokine production.

Immunogenic Nucleic Acids

This document provides methods and materials related to isolated nucleic acid molecules that can be immunogenic oligonucleotides. The term "nucleic acid" as used herein encompasses both RNA and DNA, including cDNA, genomic DNA, synthetic (e.g., chemically synthesized) DNA, and nucleic acids having modified backbones, such as phosphorothioate nucleic acids, peptide nucleic acids, and morpholinos. The nucleic acid can be double-stranded or single-stranded. Where single-stranded, the nucleic acid can be the sense strand or the antisense strand. In some cases, the nucleic acid can be circular or linear. As provided herein, an isolated nucleic acid can be about 8-84 nucleotides in length (e.g., about 8-15, 8-20, 9-20, 10-20, 11-25, 12-27, 15-30, 16-35, 18-35, 20-40, 20-45, 21-46, 22-47, 23-48, 24-49, 25-50, 30-50, 40-60, 45-65, 50-64, 50-70, 55-70, 55-75, 60-74, 65-60, 65-74, or 70-84 nucleotides). In some cases, the isolated nucleic acid can be about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, or 84 nucleotides in length.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. An isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence. It will be apparent to those of skill in the art that a natural nucleic acid existing among hundreds to millions of other nucleic acid molecules within, for example, cDNA or genomic libraries, or gel slices containing a genomic DNA restriction digest, is not to be considered an isolated nucleic acid.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence. It will be apparent to those of skill in the art that a non-naturally-occurring nucleic acid existing among hundreds to millions of other nucleic acid molecules within, for example, cDNA or synthetic nucleic acid libraries is not to be considered an isolated nucleic acid.

The isolated nucleic acids provided herein can have nucleotide sequences derived from a mammalian retroviral genome. For example, isolated nucleic acids can be synthesized to have sequences derived from the HIV-1 viral genome or from the SIV viral genome. An exemplary retroviral genome for the methods and materials provided herein can be the 9719-nucleotide full-length genome of the HIV-1 HXB2 strain (GenBank Accession No. K03455). The HXB2 strain is the most infectious HIV in North America and Europe, and is widely used as a reference strain. See, e.g., Korber et al. (Eds), Human retrovirus and AIDS 1998: A compilation and analysis of nucleic and amino acid sequences, Los Alamos National Laboratory, USA (1998). In some cases, a retroviral genome can be the full-length genome of the Sykes strain of SIV. In some cases, the isolated nucleic acids provided herein can have nucleotide substitutions or modifications relative to a retroviral genome (e.g., the HIV-1 viral genome). For example, an isolated nucleic acid can have mononucleotide (e.g., T) or dinucleotide (e.g., TT) substitutions adjacent to a CG motif or "core." Isolated nucleic acids can be selected based on the number of "CG" cores within a 24-mer sequence and the flanking sequence surrounding each "CG" core. For example, isolated nucleic acids can have 1, 2, 3, 4, 5, or more "CG" cores.

Modifications or substitutions to increase or decrease the immunostimulatory activity of a nucleic acid having CpG core can include modification of nucleotides within several nucleotides (e.g., 1, 2, 3, 4, or 5 nucleotides) 5' and within several nucleotides (e.g., 1, 2, 3, 4, or 5 nucleotides) 3' of a CpG core (i.e., those nucleotides "adjacent to" the core). Modifications can be made according to the anticipated immunostimulatory effect of individual nucleotides. For example, the ranking of individual nucleotides, in order of decreasing impact, can be as follows: T>A>C>G. For RNA, the order can be as follows: U>A>C>G. In view of this ranking, an isolated nucleic acid with sequence derived from a retroviral genome (e.g., the HIV-1 genome) as described herein can be modified by, for example, substituting G with T. Such a modification can enhance the stimulatory effect of the modified ODN, relative to its unmodified counterpart, while substituting T with G can decrease the stimulatory effect. Isolated nucleic acids, therefore, can be selected according to the number of "CG" cores and the flanking sequence surrounding each "CG" core. Exemplary modifications of isolated nucleic acids derived from HIV-1 and SIV retroviral genomes are described in Examples 4 and 5, respectively.

The isolated nucleic acids can be relatively resistant to degradation by, for example, endonucleases and exonucleases. Secondary structures (e.g., stem loops, palindromic sequences) can be used as stabilizing elements to stabilize the nucleic acids against such degradation. Nucleic acid stabilization can be accomplished via phosphate backbone modifications. To this end, a stabilized ODN can have at least a partial phosphorothioate-modified backbone, which may be significant to the viral entry-blocking activity described herein. See Luganini et al., *Antimicrob Agents Chemother.* 52(3):1111-20 (2008). The pharmacokinetics of phosphorothioate ODNs have demonstrated a systemic half-life of approximately 48 hours in rodents, generally suggesting the utility of backbone-modified ODNs for in vivo applications. See, for example, Agrawal et al., *Proc. Nat'l Acad. Sci. USA* 88:7595-99 (1991).

Phosphorothioates can be synthesized via automated techniques that employ phosphoramidate or H-phosphonate chemistries. Aryl- and alkyl-phosphonates can be synthesized as described, for example, in U.S. Pat. No. 4,469,863. Alkylphosphotriesters, in which the charged oxygen moiety is alkylated, can be prepared by automated solid-phase synthesis using commercially available reagents. Any other appropriate method for modifying a nucleic acid backbone and making substitutions can be used. See, for example, modification methods described by Uhlmann and Peyman, Chem. Rev. 90:543-84 (1990); Goodchild, *Bioconjugate Chem.* 1(3):165-87 (1990); and U.S. Pat. Nos. 7,105,495 and 7,176,296.

Any appropriate method including, without limitation, common molecular cloning and chemical nucleic acid synthesis techniques can be used to obtain isolated nucleic acid molecules. For example, isolated nucleic acids can be chemically synthesized, either as a single nucleic acid molecule or as a series of oligonucleotides. In some cases, oligonucleotides can be synthesized de novo using any of a number of procedures widely available in the art. Exemplary methods of synthesis can include the β-cyanoethyl phosphoramidite method (Beaucage et al., *Tet. Let.* 22:1859-1862 (1981)) and nucleoside H-phosphonate method (Garegg et al., *Tet. Let.* 27:4051-4054 (1986); Froehler et al., *Nucl. Acid Res.* 14:5399-5407 (1986); Garegg et al., *Tet. Let.* 27:4055-4058 (1986); and Gaffney et al., *Tet. Let.* 29:2619-2622 (1988)). These methods can be performed by a variety of commercially-available automated oligonucleotide synthesizers. Alternatively, recombinant nucleic acid techniques, including restriction enzyme digestion and ligation of existing nucleic acid sequences (e.g., genomic DNA or cDNA), can also be used to isolate a nucleic acid molecule provided herein. In some cases, isolated nucleic acids can be obtained using the polymerase chain reaction (PCR). PCR refers to a procedure or technique in which target nucleic acid is amplified in a manner similar to that described in U.S. Pat. No. 4,683,195, and subsequent modifications of the procedure described therein. General PCR techniques are described, for example, in *PCR Primer: A Laboratory Manual*, Dieffenbach & Dveksler, Eds., Cold Spring Harbor Laboratory Press, 1995. Generally, sequence information from the ends of the region of interest or beyond are used to design oligonucleotide primers that are identical or similar in sequence to opposite strands of a potential template to be amplified. Any appropriate oligonucleotide primer can be used.

In some cases, the immunogenic oligonucleotides provided herein can have detectable labels or probes attached. Such detectable labels can permit detection in the presence of a complementary sequence based on detection of a bound label. Administration and detection of detectable immunogenic oligonucleotides may be useful for diagnosing certain diseases that are caused or exacerbated by particular nucleic acid sequences (e.g., systemic lupus erythematosus, sepsis, autoimmune diseases).

Methods of Using Immunogenic Oligonucleotides

This document also provides methods and materials for stimulating an immune response. In some cases, the isolated nucleic acids provided herein can be used to induce or amplify an innate immune response. For example, induction or amplification of an immune response results from Th1-type activation. Accordingly, the isolated nucleic acids can serve as oligonucleotide immunogens and can be administered to a mammal (e.g., a human subject) in an amount effective for inducing or amplifying such an immune response. Other exemplary mammals for the methods and materials provided herein can include, without limitation, non-human primates, horses, cows, goats, dogs, cats, rabbits, rats, and mice.

In some cases, isolated nucleic acids can be used to stimulate lymphocyte cytokine production. For example, a method for stimulating lymphocyte cytokine production can include contacting lymphocytes with an isolated nucleic acid provided herein. Isolated nucleic acids appropriate for such a method can have the exact sequences provided herein. In some cases, isolated nucleic acids appropriate for such a method can have any additional sequence, e.g., at least one additional CpG core sequence and/or a stabilizing sequence. For example, additional nucleotide sequence, e.g., a retroviral sequence having at least one CpG core, can be added to either terminus of an isolated nucleic acid provided herein. Stimulation of lymphocyte cytokine production according to the methods provided herein can be in vivo or in vitro.

In some cases, the isolated nucleic acids can be administered to a mammal in order to address an immune system deficiency. For example, the oligonucleotide immunogens provided herein can be used to enhance or restore innate and antigen-specific acquired immune responses in mammals with impaired immune systems, such as those infected by HIV-1. Enhancing or restoring an immune response according to the methods provided herein can provide a mode of eradicating latent HIV in infected mammals treated with antiviral therapy. In some cases, the methods can be used to suppress viral transmission in mammals considered to be at high risk for becoming infected.

Isolated nucleic acids provided herein can be used as oligonucleotide immunogens and administered to a mammal for therapeutic or prophylactic purposes. For example, the oligonucleotide immunogens can be administered to a mammal in order to treat or prevent a viral infection, retroviral infection, bacterial infection, or parasitic infection. An immunogenic oligonucleotide can be used to block virus entry, thereby aiding in the elimination of the virus. In some cases, isolated nucleic acids can be administered as a therapeutic immunogen (e.g., a vaccine adjuvant) for the prevention or treatment of an allergy or for anti-cancer therapy. In some cases, a method of treating or preventing can include administering an isolated nucleic acid provided herein to a mammal having or at risk of having such an infection in an amount effective for treating or preventing infection of the mammal. Infections suitable for the methods and materials provided herein can include infection by hepatitis virus, HIV, hepatitis B, hepatitis C, herpes virus, papilloma virus, intracellular bacteria (e.g., *Mycobacterium tuberculosis*), and intracellular parasites, in particular non-helminthic parasites. Other exemplary medical conditions for which the isolated nucleic acids can be used can include microbial infections (e.g., sexually transmitted disease), fungal diseases (e.g., candidiasis), or parasitic diseases including, without limitation, malaria, pneumocystis camii pneumonia, leishmaniasis, cryptosporidiosis, and toxoplasmosis.

In some cases, the isolated nucleic acids potentially can be used to decrease a mammal's immune response. For example, isolated nucleic acids can have modifications that suppress CpG-mediated cytokine induction in a mammal. Such isolated nucleic acids likely can be used for immunomodulation in a mammal having an autoimmune disease or symptoms associated with enhanced cytokine production. In some cases, such isolated nucleic acids can be administered to a mammal in order to decrease or suppress overstimulation of an immune response such as in the case of an autoimmune disease, allergic reaction, asthma, or anaphalaxis. Exemplary autoimmune diseases appropriate for the methods and materials provided herein can include, without limitation, lupus erythematosus, Addison's disease, alopecia, Guillain Barré syndrome, celiac disease, Crohn's disease, and multiple sclerosis.

For administration in vivo, immunogenic oligonucleotides can be associated with a molecule that results in higher affinity binding to target cell (e.g., B-cell, NK cell) surfaces and/or increased cellular uptake by target cells to form an "oligonucleotide delivery complex." The immunogenic oligonucleotides provided herein can be ionically or covalently associated with appropriate molecules using techniques that are well known in the art. A variety of coupling or crosslinking agents can be used (e.g., protein A, carbodiimide, N-succinimidyl-3-(2-pyridyldithio)propionate (SPDP)). The immunogenic oligonucleotides alternatively can be encapsulated in liposomes or virosomes using well-known techniques. For anti-cancer therapy, immunogenic oligonucleotides can be administered to a mammal prior to chemotherapy in order to increase responsiveness of the malignant cells to subsequent chemotherapy and/or to induce natural killer (NK) cell activity.

Evaluating Immunomodulatory Activity

The immunogenic oligonucleotides can be used to stimulate lymphocytes to produce an immune response as determined by stimulated cytokine production. In some cases, the oligonucleotides can be used to suppress lymphocytes to decrease or suppress an immune response as determined by reduced cytokine production. The activity of the isolated nucleic acids for modulation of the immune response (e.g., lymphocyte stimulatory activity) can be evaluated by any appropriate methods. For example, immunomodulatory activity can be measured in assays evaluating cytokine production/release, including those described in the Examples below. In some cases, peripheral blood mononuclear cells (PBMCs) can be used to evaluate stimulation of an immune response. In some cases, immunomodulatory capacity of the isolated nucleic acids can be evaluated using a TLR-9 antagonism assay. In such an assay, the Namalwa cell line, a human lymphoblastoid cell line derived from a child with a Burkitt's lymphoma, can be used to evaluate stimulation of cytokine (e.g., IL-6, IL-10, and TNF-$\alpha$) production. Generally, immunosuppressive oligonucleotides (TLR-9 antagonists) can inhibit TLR-9 agonist-induced cytokine production in a dose-dependent manner. By contrast, immunostimulatory oligonucleotides (TRL-9 agonists) can stimulate immune activation in Namalwa cells as determined by stimulation of inflammatory cytokine production. Direct and indirect CpG ODN-induced cytokine secretion occurs in a variety of cell types, including B lymphocytes, monocytes, macrophages, dendritic cells, natural killer cells, and even mast cells. Depending on the cell type activated, they proliferate, upregulate MHC class I and II, B7-1 and B7-2 co-stimulatory molecules, or express a broad range of cytokines including IL-1, IL-6, IL-10, IL-12, IFN-$\alpha$, IFN-$\gamma$, and TNF-$\alpha$.

In some cases, immunomodulation can be evaluated by detecting inflammatory cytokine release by dendritic cells, lymphocytes, macrophages, T cells, or other immune system cells. Secretion of cytokines such as IL-12, IL-6, IL-1b, IL-10, and TNF-$\alpha$, can be measured, for example, by an enzyme linked immunosorbent assay (ELISA). Activation of naïve T-cells can be assayed by, for example, measuring the incorporation of $^3$H-thymidine into newly synthesized DNA in proliferating cells, by measuring induction of cytolytic T-cell activity, or by detecting T-cell activation markers (e.g., CD44 or CD69). In some cases, expression or translocation of NF-$\kappa$B can be measured by, for example, cell staining with an antibody against NF-$\kappa$B. Antibodies against NF-$\kappa$B are available from, for example, Cell Signaling Technologies, Inc. (Beverly, Mass.).

Any appropriate method can be used to evaluate an individual's immune response following administration of an adjuvant containing at least one isolated nucleic acid as described herein. For example, a biological sample from an individual can be examined to evaluate the immune response in vitro. The biological sample can be blood (e.g., whole blood or serum), blood cells (e.g., lymphocytes, monocytes, eosinophils, or basophils), or a mucosal sample (e.g., saliva or gastric and bronchoalveolar lavages). In some cases, biological samples are collected prior to and after administration of a nucleic acid as described herein.

Preparing Immunogenic Oligonucleotide Compositions

This document also provides methods and materials for obtaining compositions containing isolated nucleic acids (e.g., an isolated nucleic acid of 8-84 nucleotides derived from a retroviral sequence). For example, isolated nucleic acids can be combined with a therapeutic antigen (e.g., an immunogenic peptide) to form a composition for administration to a mammal. Suitable therapeutic antigens include, for example, polypeptides or fragments of polypeptides expressed by tumors and pathogenic organisms. Examples of therapeutic antigens include, without limitation, propionyl CoA carboxylase (NM_000282), dystrophin (M92650), p53 (M14695), factor IX (BC109215), herpes virus thymidine kinase (NC_001798), measles H and F fusogenic glycoproteins (DQ227321), sodium iodide symporter (NM_000453), and heat shock protein (L12723). Thus, the isolated nucleic acids can be used to generate immunostimulatory compositions. Such a composition generally contains at least one isolated nucleic acid as described herein. A composition can be used as an adjuvant to stimulate a mammal's immune response, typically against an antigen. Compositions can be administered by any route that permits uptake of the oligonucleotides by the appropriate target cells. Exemplary routes of administration can include administration to mucosal surfaces. Mucosal surfaces include, for example, intranasal, oral, parenteral, rectal, and vaginal surfaces and, accordingly, compositions can be administered by a route including intranasally, orally, transdermally, gastrointestinally, rectally, vaginally, or via the genitourinary tract. In some cases, immunogenic oligonucleotides can be administered by injection (e.g., subcutaneous, intravenous, parenteral, intraperitoneal, intrathecal). Administration by injection can involve a bolus or continuous infusion of a composition.

In some cases, the isolated nucleic acids can be formulated into pharmaceutical compositions using techniques and procedures well known in the art (see, e.g., Ansel, Introduction to Pharmaceutical Dose Forms, Fourth Edition 1985, 126). For example, a composition can be administered with a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with the intended route of administration. For example, pharmaceutical preparations such as sterile solutions or suspensions can be used to make compositions suitable for parental administration. Pharmaceutically acceptable carriers can also include a solid, semi-solid, or liquid material that acts as a vehicle, carrier, or medium for the isolated nucleic acids provided herein. The use of such pharmaceutically acceptable carriers with compositions is well known in the art. Except insofar as any conventional pharmaceutically acceptable carrier is incompatible with the active compound, use thereof in any of the compositions described herein is contemplated.

Compositions can contain therapeutically effective amounts of one or more of the isolated nucleic acids and a pharmaceutically acceptable carrier. Typically, an adjuvant is administered to a mammal such that the mammal produces a greater immune response toward an antigen compared to the immune response produced toward the antigen in the absence of the adjuvant. A suitable amount of an adjuvant is one that increases an immune response in a mammal but does not result in significant toxicity. A suitable amount of an adjuvant can depend on factors such as, without limitation, the route of administration; the nature of the composition; the weight of the mammal; the particular antigen; and the concurrent administration of other vaccines or drugs. A suitable amount of an adjuvant can be established by one of ordinary skill in the art through routine trials establishing dose response curves. For example, a therapeutically effective concentration may be determined empirically by testing the isolated nucleic acids in in vitro and in vivo systems, and then extrapolating therefrom for doses for humans or other subjects.

For therapeutic indications, immunostimulatory doses can range, for example, from about 1 µg to about 10 mg and, more typically, can range from about 10 µg to 1 mg oligonucleotides per administration of the active agent. Doses can be administered, for example, daily or weekly. Doses for parenteral delivery of a therapeutic composition can range, for example, from about 0.1 µg to about 10 mg oligonucleotides per administration which could be given daily, weekly, monthly, or according to any other appropriate dosing schedule. More typically, parenteral doses can range, for example, from about 10 µg to about 5 mg oligonucleotides per administration, and most typically from about 100 µg to 1 mg oligonucleotides, with about 2-4 administrations being spaced days or weeks apart.

In some cases, a composition of isolated nucleic acids as described herein can be administered with one or more additional components. For example, the composition can be administered with a penetration enhancer to promote the efficient delivery to a mucosal surface of an adjuvant provided herein. For example, a penetration enhancer can be a surfactant (e.g., sodium lauryl sulfate, polyoxyethylene-9-lauryl ether and polyoxyethylene-20-cetyl ether); a fatty acid (e.g., oleic acid, lauric acid, myristic acid, palmitic acid, and stearic acid); a bile salt (e.g., cholic acid, dehydrocholic acid, and deoxycholic acid); a chelating agent (e.g., disodium ethylenediamine tetraacetate, citric acid, and salicylates); or a non-chelating non-surfactant (e.g., unsaturated cyclic urea).

In some cases, methods for solubilizing components of a pharmaceutical composition can be used. Such methods are known to those of skill in this art, and include, but are not limited to, using cosolvents, such as dimethylsulfoxide (DMSO), polyethylene glycol (PEG) (e.g., PEG400), cyclodextrins or cremaphor; using surfactants, such as TRITON® X-100 detergent (Union Carbide Corp.) or TWEEN® polysorbate surfactant (Croda International PLC), or dissolution in aqueous sodium bicarbonate.

Pharmaceutical compositions can be provided for administration to humans and animals in unit dose forms, such as sterile parenteral solutions or suspensions, containing suitable quantities of the nucleic acids provided herein. In some cases, the compositions can be formulated and administered in unit-dose forms or multiple-dose forms. The term "unit-dose form" refers to physically discrete units suitable for human and animal subjects and packaged individually as is known in the art. Each unit-dose form contains a predetermined quantity of the therapeutically active compound sufficient to produce the desired immunomodulatory effect, in association with any necessary pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dose forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, and the like, to thereby form a solution or suspension. If the composition is to be administered intravenously, suitable carriers can include physiological saline or phosphate buffered saline (PBS), and solutions containing thickening and solubilizing agents, such as glucose, polyethylene glycol, and polypropylene glycol and mixtures thereof. In some cases, the composition to be administered can also include non-toxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Any appropriate method of preparing such dose forms can be used. For example, dose forms can be prepared according to the methods provided in Remington's Pharmaceutical Sciences, Mack Publishing Company, Easton, Pa., 15th Edition, 1975.

Articles of Manufacture

This document also provides methods and materials for providing the immunogenic oligonucleotides or pharmaceutical compositions described herein as articles of manufacture (e.g., kits) containing packaging material, an immunogenic oligonucleotide within the packaging material, and a label that indicates that the immunogenic oligonucleotide or composition is useful for stimulating an immune response, or for the treatment or prevention of viral infections, bacterial infections, or allergic response.

The articles of manufacture provided herein contain packaging materials. Packaging materials for use in packaging pharmaceutical products are well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

The invention will be further described in the following examples, which do not limit the scope of the invention described in the claims.

EXAMPLES

Example 1

Synthesis of HIV-Derived ODNs

Analysis of the 9719-nucleotide HXB2 genome revealed 94 CpG dinucleotide motifs or "cores" distributed throughout the genome between positions 24 to 9650. The cores were numbered according to the scheme described in Korber et al., available at hiv.lanl.gov/content/sequence/HIV/REVIEWS/HXB2.html on the World Wide Web. In view of this distribution, twenty-five ODNs were constructed using conventional synthesis methodology described previously. See, for example, Stein et al., *Nucleic Acids Res.* 16:3209-3221 (1988). The ODNs were designed according to CpG-containing portions of the genome of the HXB2 strain of HIV-1. Each of the resultant ODNs was 24 nucleotides long. Sequences of the 25 HIV-derived ODNs (S1-S25) are presented in Table 1. The corresponding portions collectively spanned the viral genome from position 24 to position 9472, and, respectively, extended into the following HIV-1 genes: gag (p17, portion 13; p24, portion 14; p7, portion 15), pol (p51, portion 16; p31, portion 17), vif (portion 18), vpu (portion 19), and env (gp120, portions 20, 21, and 22; gp41, portions 23 and 24). Portions 1-13 and 25 also extended into with 5' LTR and 3' LTR, respectively.

TABLE 1

Sequences of HIV-Derived CpG Oligonucleotides

| Name | Core Position | Sequences | |
|---|---|---|---|
| S1 | BTI-HXB2-CG24 | TTCACTCCCAACGAAGACAAGATA | (SEQ ID NO: 1) |
| S2 | BTI-HXB2-CG238 | AATGGATGACCCGGAGAGAGAAGT | (SEQ ID NO: 2) |
| S3 | BTI-HXB2-CG273 | GGTTTGACAGCCGCCTAGCATTTC | (SEQ ID NO: 3) |
| S4 | BTI-HXB2-CG336 | ACTGCTGACATCGAGCTTGCTACA | (SEQ ID NO: 4) |
| S5 | BTI-HXB2-CG359 | AAGGGACTTTCCGCTGGGGACTTT | (SEQ ID NO: 5) |
| S6 | BTI-HXB2-CG408 | CTGGGGAGTGGCGAGCCCTCAGAT | (SEQ ID NO: 6) |
| S7 | BTI-HXB2-CG565 | TAGTGTGTGCCCGTCTGTTGTGTG | (SEQ ID NO: 7) |
| S8 | BTI-HXB2-CG639 | TCTAGCAGTGGCGCCCGAACAGGG | (SEQ ID NO: 8) |
| S9 | BTI-HXB2-CG687 | AGGAGCTCTCTCGACGCAGGACTC | (SEQ ID NO: 9) |
| S10 | BTI-HXB2-CG728 | ACGGCAAGAGGCGAGGGGCGGCGA | (SEQ ID NO: 10) |
| S11 | BTI-HXB2-CG751 | ACTGGTGAGTACGCCAAAAATTTT | (SEQ ID NO: 11) |
| S12 | BTI-HXB2-CG832 | GAGAATTAGATCGATGGGAAAAAA | (SEQ ID NO: 12) |
| S13 | BTI-HXB2-CG921 | CTAGAACGATTCGCAGTTAATCCT | (SEQ ID NO: 13) |
| S14 | BTI-HXB2-CG1766 | GGTCCAAAATGCGAACCCAGATTG | (SEQ ID NO: 14) |
| S15 | BTI-HXB2-CG2274 | CTCTTTGGCAACGACCCCTCGTCA | (SEQ ID NO: 15) |
| S16 | BTI-HXB2-CG2840 | ATACCACATCCCGCAGGGTTAAAA | (SEQ ID NO: 16) |
| S17 | BTI-HXB2-CG4603 | CACCGGTGCTACGGTTAGGGCCGC | (SEQ ID NO: 17) |
| S18 | BTI-HXB2-CG5540 | GCCTAGTGTTACGAAACTGACAGA | (SEQ ID NO: 18) |
| S19 | BTI-HXB2-CG6063 | AGTACATGTAACGCAACCTATACC | (SEQ ID NO: 19) |
| S20 | BTI-HXB2-CG6656 | AATAGTAGTAGCGGGAGAATGATA | (SEQ ID NO: 20) |
| S21 | BTI-HXB2-CG7146 | GAAAAAGAATCCGTATCCAGAGAG | (SEQ ID NO: 21) |
| S22 | BTI-HXB2-CG7342 | AGAAATTGTAACGCACAGTTTTAA | (SEQ ID NO: 22) |
| S23 | BTI-HXB2-CG8371 | TTCACCATTATCGTTTCAGACCCA | (SEQ ID NO: 23) |
| S24 | BTI-HXB2-CG8414 | CCCGACAGGCCCGAAGGAATAGAA | (SEQ ID NO: 24) |
| S25 | BTI-HXB2-CG9421 | ACTGCTGACATCGAGCTTGCTACA | (SEQ ID NO: 25) |

Example 2

Namalwa Cellular Assay

Namalwa cells, which tend to exhibit strong immunoresponses (e.g., cytokine release) following ODN treatment, were obtained from the American Type Culture Collection (Manassas, Va.). The Namalwa cell line was maintained in RPMI medium supplemented with 10% fetal bovine serum. Cells were maintained in a humidified incubator at 37° C. with 90% relative humidity and 5% $CO_2$.

Prior to each experiment, cells were seeded at a concentration of $1 \times 10^6$ cells/mL in 24-well cell culture plates. The cells were treated with different concentrations of one of the 25 ODNs (0.25 μM to 0.5 μM). Supernatants were collected after 8-hour to 48-hour incubations with the ODN and analyzed for Interleukin-10 (IL-10), Interleukin-6 (IL-6), and Tumor Necrosis Factor-α (TNF-α) production, respectively, using an ELISA MAX™ detection kit (BioLegend, San Diego, Calif.).

Figure 2:
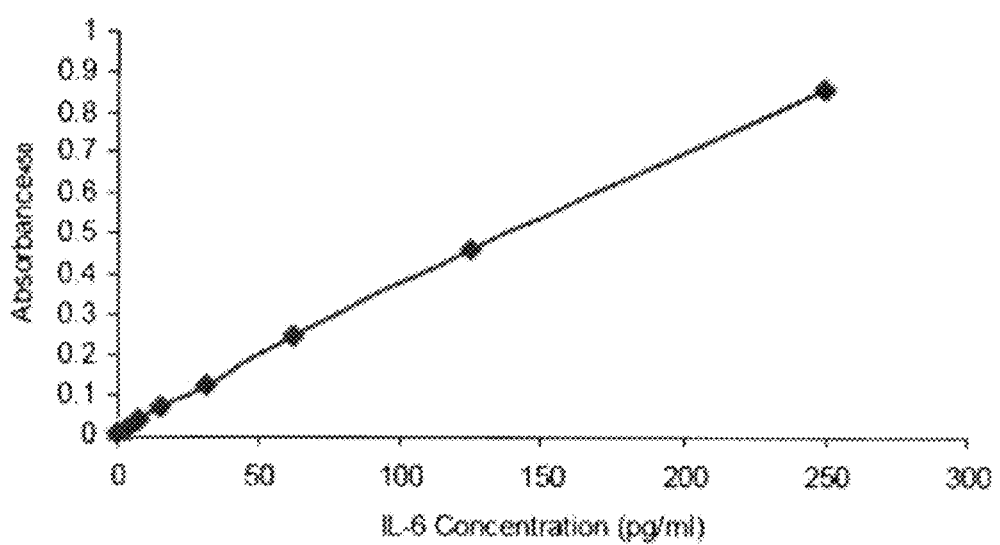
FIG. 2 is a graph exemplifying standard measurement curves (absorbance vs. concentration) for Interleukin-6 (IL-6), with respect to an ELISA for monitoring the immune response of Namalwa cells in vitro.
Figure 3:
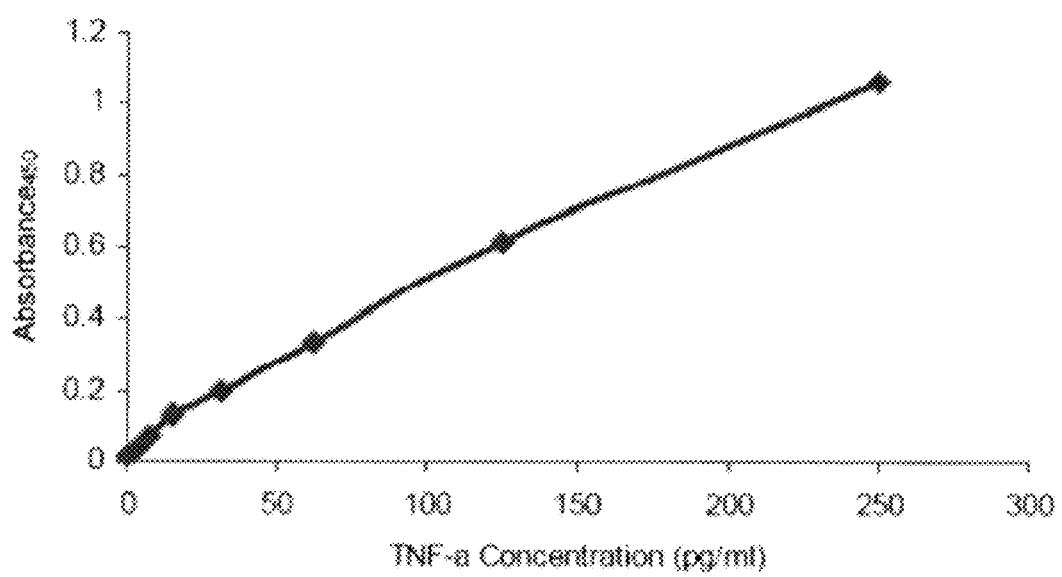
FIG. 3 is a graph exemplifying standard measurement curves (absorbance vs. concentration) for Tumor Necrotic Factor-α (TNF-α), with respect to an ELISA for monitoring the immune response of Namalwa cells in vitro.
Figure 4:
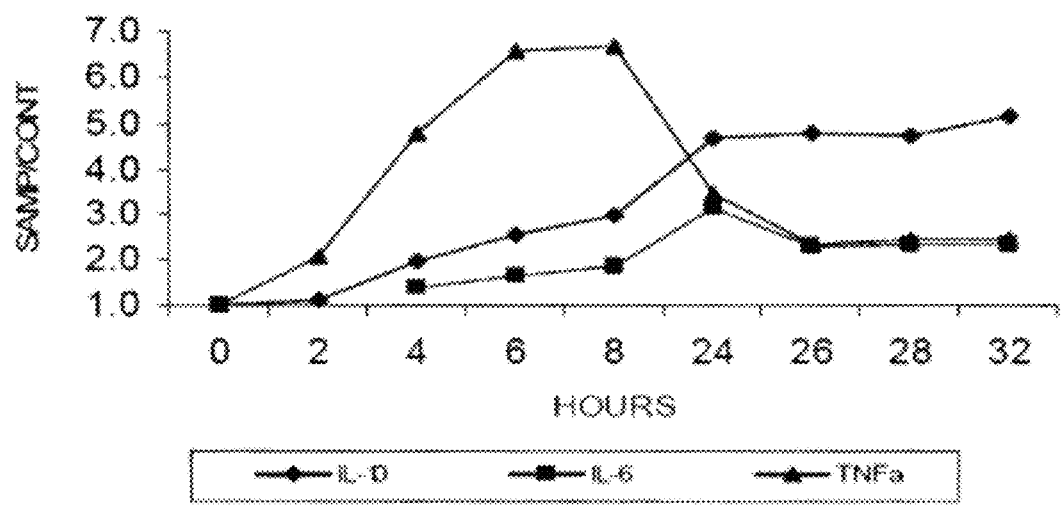
FIG. 4 is a graph showing time-course curves for cytokines IL-10, IL-6, and TNF-α according to the immune response elicited by CpG ODN in Namalwa cells.

With cytokine values thus determined, standard curves for each of IL-10, IL-6, and TNF-α measurement were established as shown in FIGS. 1, 2, and 3, respectively. The ability to detect all three cytokines simultaneously was also confirmed, as demonstrated in FIG. 4. For example, the peak concentration of TNF-α was detected following 8 hours of ODN incubation. IL-6 concentration peaked following 24 hours of ODN incubation, while IL-10 peaked following 32 hours of ODN incubation.

Figure 5:
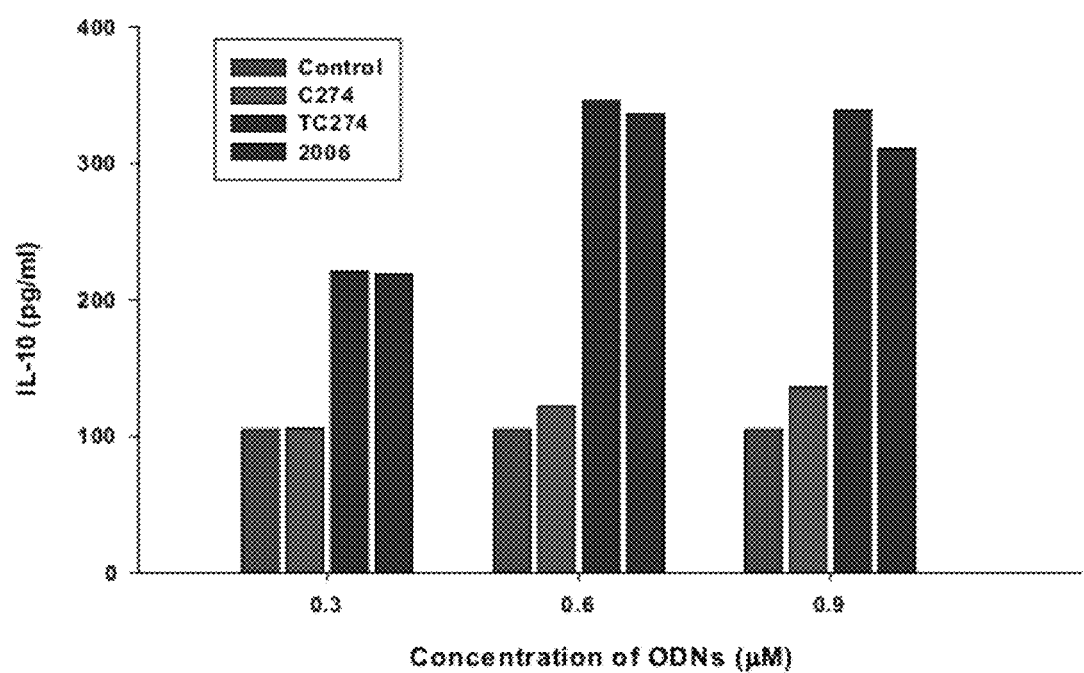
FIG. 5 is a bar graph depicting the level of IL-10 production by Namalwa cells after treatment with control (no ODN), ODN 2006, ODN C274, and ODN T-C274.

As a preliminary experiment, Namalwa cells were assayed for stimulation of IL-10 production following treatment with control ODNs and an ODN having thymidine substitutions. The cells were treated with the following ODNs as described above: ODN CpG-2006 (5'-TCGTCGTTTTGTCGTTTTGTCGTT-3' (SEQ ID NO:27)); ODN C274 (5'-TCGTCGAACGTTCGAGATGAT-3' (SEQ ID NO:100)); and ODN T-C274 (5'-TCGTGCAAGCTTG-CAGATGAT-3' (SEQ ID NO:101)). As demonstrated in FIG. 5, thymidine substitutions in ODN C274 dramatically enhanced IL-10 production, which is equal to or higher than IL-10 production following treatment with ODN 2006. It was also determined that the optimal concentration for T-C274 was 0.6 μM.

Example 3

Determination of Preferred ODN Length

Figure 6:
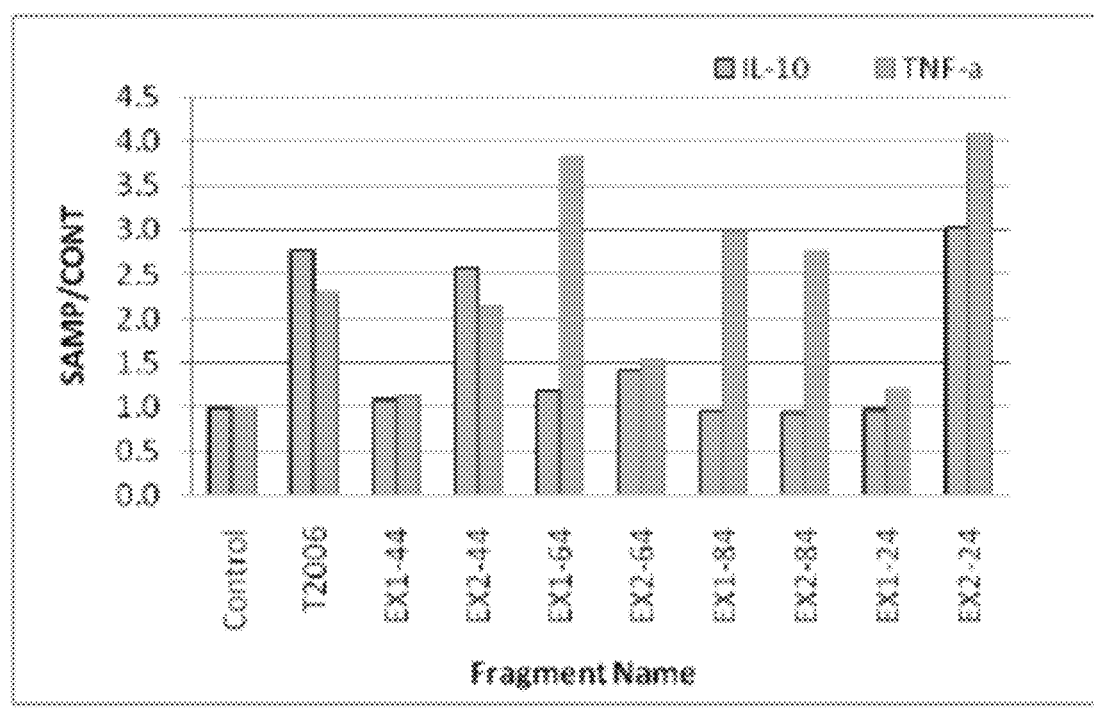
FIG. 6 is a bar graph depicting IL-10 and TNF-α production by Namalwa cells treated with DNA fragments of different length.

To determine the preferred DNA fragment length for cytokine stimulation with HIV derived oligonucleotides, two groups of DNA sequences were designed, EX1 and EX2, based on the HIV genome (Table 2). ODNs having 24, 44, 64, and 84 nucleotides were tested (Table 2). EX1-24 is homologous to ODN 2006 but does not contain a CG core. EX1-44, EX1-64, and EX1-84 are different extensions of EX1-24. Each fragment contained 44, 64, and 84 bases, respectively. EX2-24 was a modified sequence of EX1-24 containing four CG cores. EX2-44, EX2-64, and EX2-84 were different extensions of EX2-24. Namalwa cells were treated with each of the ODNs at a concentration of 0.5 μM, and cultured supernatants were collected for measurement of TNF-α and IL-10 by ELISA. As seen in FIG. 6, EX1 fragments with short length (24 and 44 bases) did not stimulate IL-10 and TNF-α production. Among the EX2 fragments, EX2-24 was the most stimulatory. Interestingly, no significant difference in stimulation was observed between cells treated with EX1-84 or EX2-84. These results indicated that the preferred ODN length for stimulating IL-10 and TNF-α cytokine release was 24 nucleotides. No direct correlation was observed between immunostimulation and ODN sequence length greater than 44 nucleotides, suggesting that specificity declines for ODNs longer than 44 nucleotides.

hours of incubation for ELISA measurements of TNF-α, and after 24 hours for measurement of IL-10 and IL-6. The concentration of each ODN was 0.5 μM. As demonstrated in FIG. 7, the HIV-derived ODNs compared favorably to ODN T2006, having the bacterially-derived sequence 5'-TCGTCGTTTTTCGTTTTTCGTT-3' (SEQ ID NO:26), where residues modified relative to ODN CpG-2006 (5'-TCGTCGTTTTGTCGTTTTGTCGTT-3' (SEQ ID NO:27)) are bolded and underscored.

Namalwa cells produced the greatest amount of IL-10 in the presence of ODN T2006. Of the HIV-derived ODNs, only S23 and S13 showed robust IL-10 production (FIG. 7A). The other HIV-derived ODNs had no effect on IL-10 production. Namalwa cells produced the greatest amount of TNF-α in the presence of ODN T2006 and HIV-derived ODN S23 (FIG. 7B). All other HIV-derived ODNs had no effect on TNF-α production. It was observed that Namalwa cells incubated with the HIV-derived ODNs produced comparable amounts of IL-6 as the control ODN (FIG. 7C). S17 and S23 showed minimal stimulation of IL-6 production. All other HIV-derived ODNs were ineffective. Overall, S23 was revealed to be the most potent cytokine stimulator of all of the HIV-derived ODNs as it demonstrated robust stimulation of all three cytokines These results demonstrate that HIV-derived ODNs having CpG motifs can be used to stimulate an immune response in vitro.

Example 5

ODNs with Modified HIV Sequence

Twenty-five ODNs having a 24-nucleotide sequence modified relative to the ODNs derived from HIV-1 sequence were

TABLE 2

Selected DNA fragments from the HIV genome

| Name | Sequences | Fragment Length (nt) |
|---|---|---|
| EX1-24 | TTATTGTTTTATTATTTCCAAATT (SEQ ID NO: 92) | 24 |
| EX1-44 | TGCTTAAAGATTATTGTTTTATTATTTCCAAATTGTTCTCTTAA (SEQ ID NO: 93) | 44 |
| EX1-64 | TCCTGAGGATTGCTTAAAGATTATTGTTTTATTATTTCCAAATT GTTCTCTTAATTTGCTAGCT (SEQ ID NO: 94) | 64 |
| EX1-84 | CTGGGTCCCCTCCTGAGGATTGCTTAAAGATTATTGTTTTATTA TTTCCAAATTGTTCTCTTAATTTGCTAGCTATCT (SEQ ID NO: 95) | 84 |
| EX2-24 | TCGTCGTTTTATCGTTTCCACGTT (SEQ ID NO: 96) | 24 |
| EX2-44 | TGCTTAAAGATCGTCGTTTTATCGTTTCCACGTTGTTCTCTTAA (SEQ ID NO: 97) | 44 |
| EX2-64 | TCCTGAGGATTGCTTAAAGATCGTCGTTTTATCGTTTCCACGTT GTTCTCTTAATTTGCTAGCT (SEQ ID NO: 98) | 64 |
| EX2-84 | CTGGGTCCCCTCCTGAGGATTGCTTAAAGATCGTCGTTTTATCGT TTCCACGTTGTTCTCTTAATTTGCTAGCTATCT (SEQ ID NO: 99) | 84 |

Example 4

HIV-Derived ODNs

To test the immunostimulatory capacity of each HIV-derived ODN, Namalwa cells were seeded at a concentration of 1×10$^6$ cells/mL in 24-well cell culture plates. Cells were incubated in the presence of HIV-derived ODNs (see Table 1), each ODN with a 24-nucleotide sequence derived from genomic DNA between position 24 and position 9472 of the HIV-1 genome. Culture supernatants were collected after 8 constructed using conventional synthesis methodology described previously. Each sequence was modified by T or A nucleotide substitution. Table 3 presents the sequences of the 25 modified ODNs (SL-1-SL-25) with the positions of all nucleotide substitutions identified (bolded and underscored). To assay for immunostimulatory activity of the modified ODNs, Namalwa cells were seeded at a concentration of 1×10$^6$ cells/mL in 24-well cell culture plates, and were incubated in the presence of the modified ODNs (SL-1-SL-25). Supernatant collection and ELISA cytokine measurements were conducted as described above.

As demonstrated in FIG. 8A, almost all HIV-modified ODNs enhanced IL-10 production relative to unmodified fragments. HIV-modified ODNs SL-10, SL-13, SL-17, and SL-24 produced the greatest amount of IL-10 relative to ODN T2006 (FIG. 8A). HIV-modified ODNs SL-10, SL-13, and SL-17 produced the greatest amount of TNF-α relative to ODN T2006 (FIG. 8B). Only SL17 stimulated more TNF-α production than T2006. HIV-modified ODNs SL-3, SL-4, SL-7, SL-10, SL-13, SL-17, SL-22, and SL-24 were the best stimulators of IL-6 production (FIG. 8C). Overall, ODNs SL-4, SL-10, SL-13, SL-17, and SL-24 were the most stimulatory for all three cytokines These results demonstrate that HIV-modified ODNs having CpG motifs can be used to stimulate an immune response in vitro.

TABLE 3

Sequences of CpG Oligonucleotides with Modified HIV Sequence

| Name | Nucleotide Sequence | |
|---|---|---|
| SL-1 | TTCACTCCCTTCGTTGACAAGATA | (SEQ ID NO: 28) |
| SL-2 | AATGGATGATTCGTTGAGAGAAGT | (SEQ ID NO: 29) |
| SL-3 | GGTTTGACATTCGTTTAGCATTTC | (SEQ ID NO: 30) |
| SL-4 | ACTGCTGACTTCGTTCTTGCTACA | (SEQ ID NO: 31) |
| SL-5 | AAGGGACTTTTCGTTGGGGACTTT | (SEQ ID NO: 32) |
| SL-6 | CTGGGGAGTTTCGTTCCCTCAGAT | (SEQ ID NO: 33) |
| SL-7 | TAGTGTGTGTTCGTTTGTTGTGTG | (SEQ ID NO: 34) |
| SL-8 | TCTAGCAGTTTCGTTCGAACAGGG | (SEQ ID NO: 35) |
| SL-9 | AGGAGCTCTTTCGTCGTAGGATTC | (SEQ ID NO: 36) |
| SL-10 | ACGTTAAGATTCGTTGTTCGTCGT | (SEQ ID NO: 37) |
| SL-11 | TTTGGTGAGTTCGTTAAAAATTTT | (SEQ ID NO: 38) |
| SL-12 | GAGAATTAGATCGTTGGGAAAAAA | (SEQ ID NO: 39) |
| SL-13 | CTAGTTCGTTTCGTTGTTAATCCT | (SEQ ID NO: 40) |

TABLE 3-continued

Sequences of CpG Oligonucleotides with Modified HIV Sequence

| Name | Nucleotide Sequence | |
|---|---|---|
| SL-14 | GGTCCAAAATTCGTTCCCAGATTG | (SEQ ID NO: 41) |
| SL-15 | CTCTTTGGCTTCGTTCCTTCGTTA | (SEQ ID NO: 42) |
| SL-16 | ATACCACATTCGTAGGGTTAAAA | (SEQ ID NO: 43) |
| SL-17 | CATCGTTGCTTCGTTTAGGTTCGT | (SEQ ID NO: 44) |
| SL-18 | GCCTAGTGTTTCGTTACTGACAGA | (SEQ ID NO: 45) |
| SL-19 | AGTACATGTTTCGTTACCTATACC | (SEQ ID NO: 46) |
| SL-20 | AATAGTAGTTTCGTTAGAATGATA | (SEQ ID NO: 47) |
| SL-21 | GAAAAGAATTCGTTTCCAGAGAG | (SEQ ID NO: 48) |
| SL-22 | AGAAATTGTATCGTTCAGTTTTAA | (SEQ ID NO: 49) |
| SL-23* | TTCACCATTATCGTTTCAGACCCA | (SEQ ID NO: 50) |
| SL-24 | TTCGTTAGGTTCGTTGGAATAGAA | (SEQ ID NO: 51) |
| SL-25 | ACTGCTGACTTCGTTCTTGCTACA | (SEQ ID NO: 52) |

*SL-23 is unmodified relative to HIV-1 derived SEQ ID NO: 23 (SL-23 = S-23)

Example 6

Education of Naïve Namalwa Cells

Naïve Namalwa cells were treated with 0.3 μM ODN CpG-2006 (SEQ ID NO:27) or 0.3 μM of an ODN 2006 variant (listed in Table 5) and allowed to incubate for 48 hours, after which IL-10 production was quantified by ELISA. As presented in Table 4, naïve cells demonstrated enhanced IL-10 production (320 pg/mL), relative to untreated cells, 48 hours after treatment with ODN 2006, while naïve cells treated with the ODN 2006 variants exhibited variable IL-10 production. It was observed that, relative to the stimulation of IL-10 following ODN 2006 treatment, none of the ODN 2006 variants activated significant IL-10 production in naïve Namalwa cells.

TABLE 4

IL-10 Production in Naïve and Educated Namalwa cells Following Incubation with ODN 2006 Variants

| Namalwa Cells | IL-10 Production* | | | | | | | |
|---|---|---|---|---|---|---|---|---|
| | ODN 2006 | ODN 2006-1 | ODN 2006-2 | ODN 2006-3 | ODN 2006-4 | ODN 2006-5 | ODN 2006-6 | ODN 2006-7 |
| Naïve | 320 | 230 | 80 | 290 | 120 | 150 | 140 | 260 |
| Educated‡ | 440 | 390 | 140 | 450 | 180 | 340 | 300 | 440 |

*IL-10 production (pg/mL) 48 hours after treatment with ODN 2006 and its variants (ODN 2006-1-ODN 2006-7).
‡Educated cells are defined as cells treated with ODN 2006 (0.3 μM) and allowed to divide for two weeks.

TABLE 5

Nucleotide Sequences of ODN 2006 Variants

| ODN 2006 | T*C*G*T*C*G*T*T*T*T*G*T*C*G*T*T*T*T*G*T*C*G*T*T | (SEQ ID NO: 27) |
|---|---|---|
| Changed area | N*C*G*N*C*G*N*N*N*N*N*N*C*G*N*N*N*N*N*N*C*G*N*N | (SEQ ID NO: 85) |
| ODN 2006-1 | C*C*G*C*C*G*T*T*T*T*G*T*C*G*T*T*T*T*G*T*C*G*T*T | |

TABLE 5-continued

Nucleotide Sequences of ODN 2006 Variants

| | | |
|---|---|---|
| Changed area | N*C*G*N*C*G*N*N*N*N*N* N*C*G*N*N*N*N*N* N*C*G*N*N | (SEQ ID NO: 86) |
| ODN 2006-2 | T*C*G*T*C*G*T*T*T*T*G* C*C*G*T*T*T*T*G* C*C*G*T*T | |
| Changed area | N*C*G*N*C*G*N*N*N*N*N*C*G* N*N*N*N*N*N*C*G* N*N | (SEQ ID NO: 87) |
| ODN 2006-3 | T*C*G*T*C*G*T*T*T*T*G*T*C*G* C*T*T*T*G*T*C*G* C*T | |
| Changed area | N*C*G*N*C*G*N*N*N*N*N* N*C*G*N*N*N*N*N* N*C*G*N*N | (SEQ ID NO: 88) |
| ODN 2006-4 | T*C*G*T*C*G*T*T*T*T*G* A*C*G*T*T*T*T*G* A*C*G*T*T | |
| Changed area | N*C*G*N*C*G*N*N*N*N*N*C*G* N*N*N*N*N*N*C*G* N*N | (SEQ ID NO: 89) |
| ODN 2006-5 | T*C*G*T*C*G*T*T*T*T*G*T*C*G* A*T*T*T*G*T*C*G* A*T | |
| Changed area | N*C*G*N*C*G*N*N*N*N* N*N*C*G*N*N*N*N* N*N*C*G*N*N | (SEQ ID NO: 90) |
| ODN 2006-6 | T*C*G*T*C*G*T*T*T*T* A*A*C*G*T*T*T*T* A*A*C*G*T*T | |
| Changed area | N*C*G*N*C*G*N*N*N*N*N*C*G*N* N*N*N*N*N*C*G*N* N | (SEQ ID NO: 91) |
| ODN 2006-7 | T*C*G*T*C*G*T*T*T*T*G*T*C*G*A* A*T*T*G*T*C*G*A* A | |

To test the effect of "priming" cells with an immunostimulatory oligonucleotide, cells treated with ODN 2006 were allowed to incubate for an additional two weeks during which time they divided normally. At the end of two weeks, the treated cells were re-introduced to ODN 2006 and introduced for the first time to seven ODN 2006 variants (Table 5), all at a concentration of 0.3 µM. The Namalwa cells appeared to be primed to the entry of ODN 2006 because IL-10 production was enhanced appreciably in all cases (Table 4). Indeed, the cells became "educated" to recognize the sequence character of ODN 2006 and were "programmed" or "primed" to recognize DNA sequences harboring a similar character (ODN 2006-1-ODN 2006-7). In other words, the variant ODNs (Table 5) boosted immune activity (IL-10 production) in educated Namalwa cells in a manner similar to ODN 2006 although they did not activate substantially IL-10 production in naïve cells.

Figure 9:
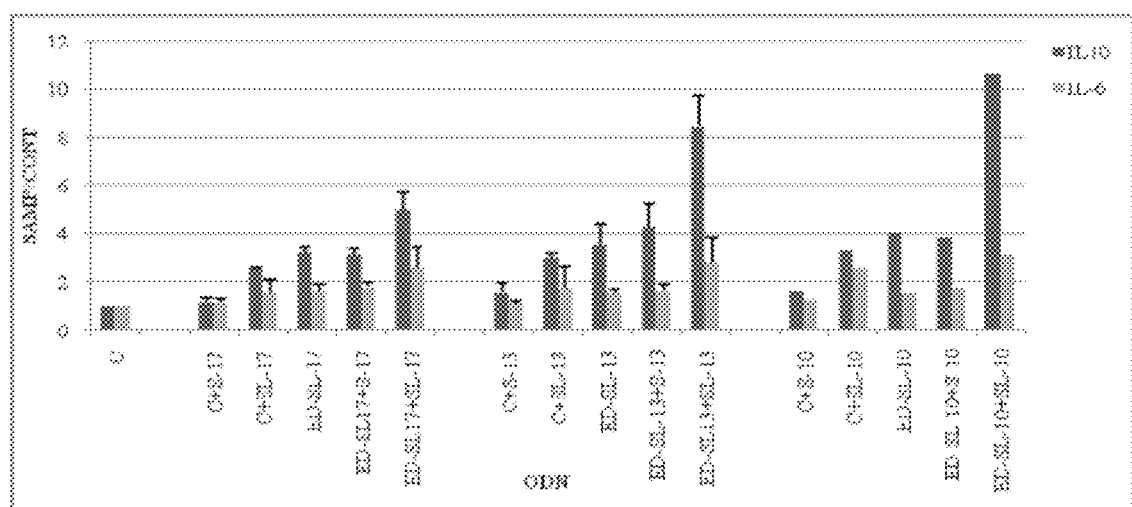
FIG. 9 is a bar graph depicting IL-10 and IL-6 cytokine production nine days after treatment with ODNs. C=control (naïve) cells; ED-SL-17, ED-SL-13 and ED-SL-10="educated" Namalwa cells. C+SL-17, C+SL-13 and C+SL-10=naïve cells treated with respective modified ODNs. C+S17, C+S13, C+S10=naïve cells treated with respective unmodified ODNs. ED-SL-17+SL17, ED-SL-13+SL-13 and ED-SL-10+SL-10=educated cells subjected to a second treatment with respective modified ODNs. ED-SL-17+S17, ED-SL-13+S13 and ED-SL-10+S10=educated cells subjected to a second treatment with respective unmodified ODNs. Data are presented as mean±SEM.

To test the response of naïve and educated Namalwa cells to HIV-modified ODNs, the above-described assays were repeated with the modified CpG ODN T2006 and HIV-modified ODNs (SL-17, SL-13, and SL-10). The treated cells were named ED-T2006, ED-SL-17, ED-SL-13 and ED-SL-10, respectively. Both naïve and treated cells were passaged according to standard cell culture methods. Nine and 21 days post-treatment, the treated cells were subjected to a second exposure and incubation with the respective CpG ODNs. Stimulation of cytokine (IL-10 and IL-6) production was measured by ELISA. As demonstrated in FIG. 9, all educated cells maintained an elevated production of IL-10 and IL-6 following the first treatment. Educated cells (ED-SL-17, ED-SL-13 and ED-SL-10) showed increased production of IL-10 and IL-6 after second treatment with the corresponding modified ODNs at nine days (FIG. 9). After the second treatment, all educated cells treated with either modified or unmodified HIV-derived ODNs showed cytokine production similar to that of naïve cells exposed to HIV-derived modified ODNs. In sum, these results suggest the Namalwa cells became "educated" to recognize the sequence character of HIV-derived ODNs.

Figure 10:
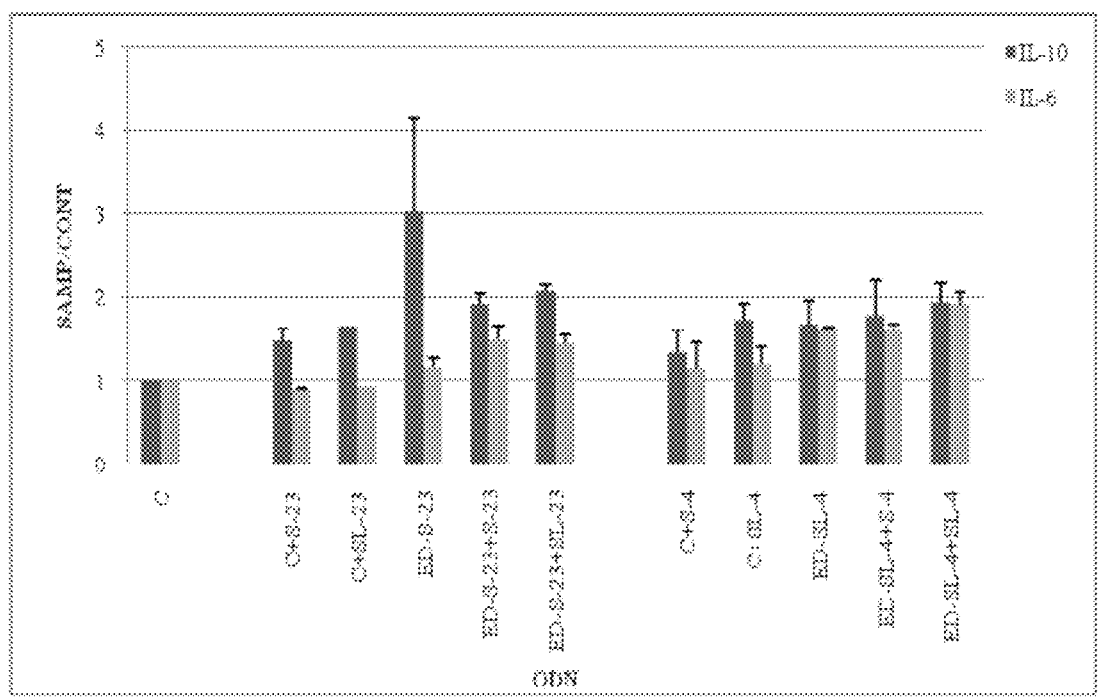
FIG. 10 is a bar graph depicting IL-10 and IL-6 cytokine production nine days after treatment with modified and unmodified HIV-1 ODNs. C=control (naïve) cells; ED-S23 and ED-SL-4="educated cells" Namalwa cells. C+S23, C+SL-23, C+S4, and C+SL4=naïve Namalwa cells treated with respective unmodified and modified ODNs. ED-S23+S23, ED-S23+SL-23, ED-SL-4+S4, and ED-SL-4+SL-4=educated Namalwa cells subjected to a second treatment with respective modified and unmodified ODNs.

To further test the response of Namalwa cells to HIV-derived ODNs, naïve and educated cells were treated with ODNs SL-4 (SEQ ID NO:31), S23 (SEQ ID NO:23), and SL-23 (SEQ ID NO:50). The ODN SL-4 was chosen because it has only one CpG island and 87.5% homology with unmodified S4. Unmodified ODN S23 was chosen because it was previously shown to stimulate cytokine production in Namalwa cells. The treated, "educated" cells were named ED-SL-4 and ED-523. Both naïve and educated cells were passaged in the normal manner. After nine days, the cells were treated again with CpG ODNs SL-23 and S23. The production of IL-10 and IL-6 cytokines was measured by ELISA. The results are presented in FIG. 10. It was observed that all educated cells maintained an elevated production of IL-10 and IL-6 on day nine following the initial exposure to SL-4 and S23. All educated cells showed increased production of IL-10 and IL-6 following a secondary exposure to the corresponding modified and unmodified ODNs.

Example 7

SIV-Derived CpG Oligonucleotides

Twenty-two CpG ODNs were synthesized based on the SIV Sykes strain genome. Each SIV-derived ODN was 24 nucleotides in length. Table 6 lists the unmodified ODN fragments (C-1-C-22) and shows the number and position of all CpG dinucleotide cores (in bold) and corresponding flanking sequences. Peripheral blood mononuclear cells (PBMCs) were isolated from monkey (*Macaca fascicularis*) blood and treated with the unmodified ODNs. Production of IL-12, TNF-α, and IL-6 was measured by ELISA as described above. As demonstrated in FIG. 11, all SIV ODNs induced IL-12 and IL-6 production in monkey lymphocytes. C-8 and C-9 induced the highest level of production of all three cytokines and production of all three was more robust than with ODN 2006. It was observed that not all ODNs stimulated production of TNF-α. For example, ODNs C-3, C-5, C-7, C-17, C-18, and C-20 exhibited no immunostimulatory effect on monkey lymphocytes as measured by stimulated TNF-αproduction.

To test the response of human cells to SIV-derived and HIV-derived ODNs, PBMCs were isolated from a human subject and treated with 22 unmodified ODNs derived from the SIV genome (C1-C22) and with 25 unmodified ODNs derived from the HIV genome (S1-S25). Production of IL-12, TNF-α, and IL-6 was measured by ELISA. Greater than 50% of the SIV-derived ODNs induced high-level production of IL-12 (FIG. 12A), TNF-α (FIG. 12B), and IL-6 (FIG. 12C) in human lymphocytes. In some cases, the level of cytokine production was greater than the cytokine production induced by ODN 2006. By comparison, only some HIV-derived ODNs induced cytokine production in human lymphocytes (FIG. 13). Overall, the response to HIV-derived ODNs was lower than that induced by ODN 2006 and much lower than the response to SIV-derived ODNs.

TABLE 6

Sequences of SIV-Derived CpG Oligonucleotides

| Name | Sequences | CG Cores |
|---|---|---|
| C-1 | AGGGTGCCATTCGTGCTAGGGTTT (SEQ ID NO: 53) | 1 |
| C-2 | GCCTGGGTGTTCGCTGGTTAGCCT (SEQ ID NO: 54) | 1 |
| C-3 | ACAGAAGCTTTCGAGGCTTGGGAT (SEQ ID NO: 55) | 1 |
| C-4 | CTCGACACGTTCGAGAAGATTAGG (SEQ ID NO: 56) | 3 |
| C-5 | GTCTCCGCGCACGTTAAATGCGTG (SEQ ID NO: 57) | 4 |
| C-6 | GCTTAGGAGTGCGTTATCATGTCT (SEQ ID NO: 58) | 1 |
| C-7 | ATAAACCTGCTCGCTTAGTCGCTA (SEQ ID NO: 59) | 2 |
| C-8 | TTGCTGAGCGTCGGAGAGGGACGA (SEQ ID NO: 60) | 3 |
| C-9 | CGCGACAGGGGCGCGGGTCCCATT (SEQ ID NO: 61) | 4 |
| C-10 | AAGCCTCGACACGTTCGAGAAGAT (SEQ ID NO: 62) | 3 |
| C-11 | CCCGTTGGAACCGACAGGCTCCGA (SEQ ID NO: 63) | 3 |
| C-12 | ATTGTCCGATCCGCTTATCGGGCA (SEQ ID NO: 64) | 3 |
| C-13 | CTCCAGACGGCCGCCGCCTGCAAG (SEQ ID NO: 65) | 3 |
| C-14 | CCCGAAGTTGGCGGTGGAGTACCG (SEQ ID NO: 66) | 3 |
| C-15 | CGGTGGAGTACCGCCCGGACATGT (SEQ ID NO: 67) | 3 |
| C-16 | TGGATCGGAGGCGGTACAGGGGCG (SEQ ID NO: 68) | 3 |
| C-17 | GCTCGCTTAGTCGCTATATTGGAG (SEQ ID NO: 69) | 2 |
| C-18 | TCGCTGGCTTGTAACTCAGTCTCT (SEQ ID NO: 70) | 1 |
| C-19 | CCGAGAGTCTTTGGCTTCTGCTTT (SEQ ID NO: 71) | 1 |
| C-20 | CCGCTAAAATGCTTTAATTGTGGC (SEQ ID NO: 72) | 1 |
| C-21 | CCAATCCGGATTGTAAATTGATTC (SEQ ID NO: 73) | 1 |
| C-22 | ACTGCAATGGGCGCAGCGGCAACA (SEQ ID NO: 74) | 2 |

Example 8

Human and Monkey Lymphocyte Response to ODNs with Unmodified HIV Sequence

A second set of CpG ODNs with unmodified HIV sequence were developed to test the cytokine response of human and monkey lymphocytes. Ten ODNs having a 24-nucleotide sequence unmodified and derived from HIV-1 sequence were constructed using the same criteria as reported before for SIV-derived ODNs. Table 7 lists the sequences of the second set of unmodified HIV-derived ODNs (SA-1-SA-10) and shows the number and position of all CpG dinucleotide cores (in bold) and corresponding flanking sequences.

Figure 14:
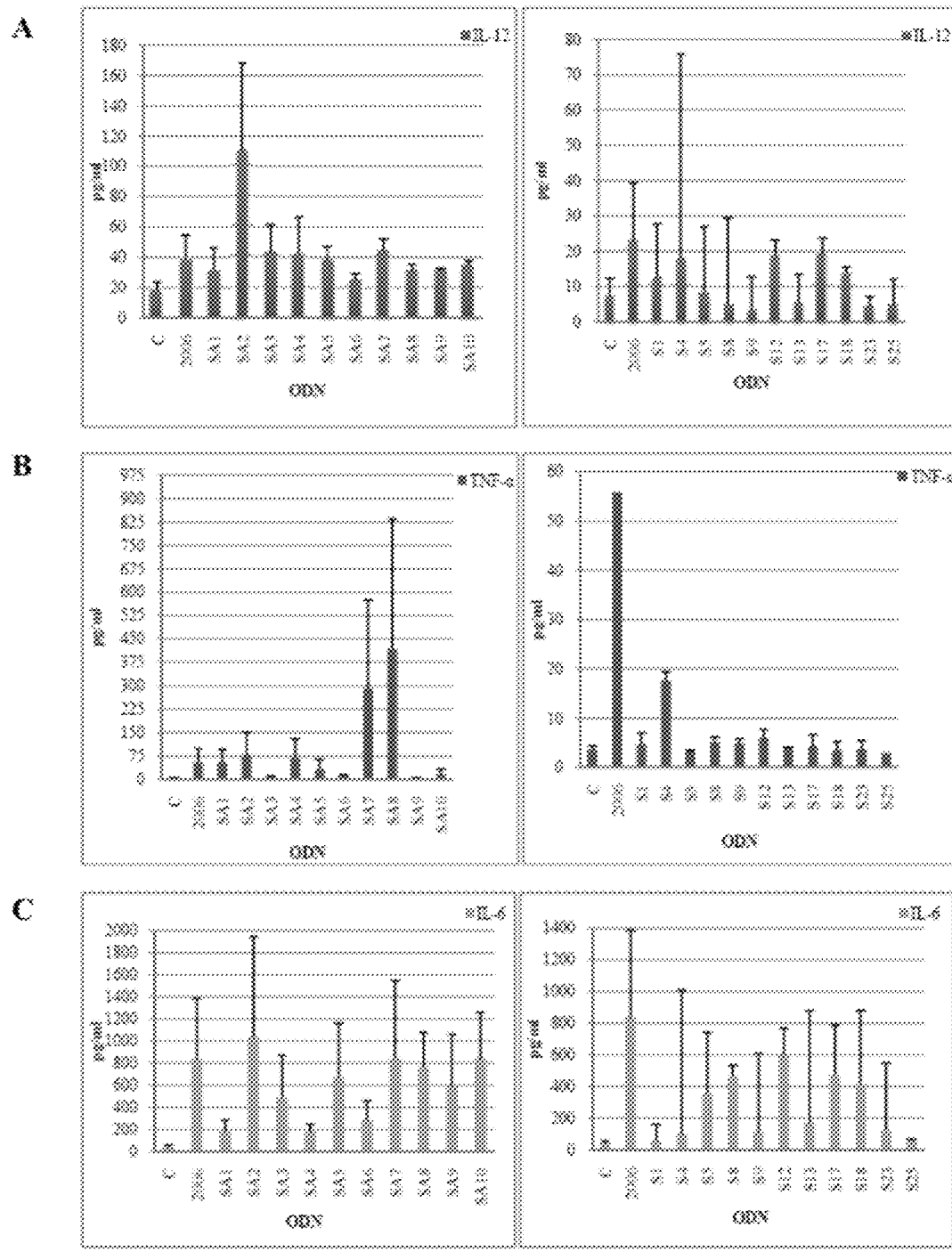
FIG. 14 presents a series of bar graphs depicting the production of cytokines IL-12 (A), TNF-α (B), and IL-6 (C) in human lymphocytes following treatment with 2 sets of HIV-derived ODNs. Data are presented as mean±SEM.

To assay the cytokine response of human lymphocytes, peripheral blood mononuclear cells (PBMCs) were isolated from human blood and treated with ODNs SA-1-SA-10 (Table 7) and with eleven previously-tested unmodified ODNs derived from the HIV genome (S1, S4, S5, S9, S12, S13, S17, S18, S23, and S25). Production of cytokines IL-12, TNF-α, and IL-6 was measured by ELISA. The results are presented in FIG. 14. It was observed that PBMC production of all three cytokines (FIG. 14) was higher in response to the ten new HIV ODNs as compared to the previously-tested ODNs.

To assay for the cytokine response of monkey lymphocytes, peripheral blood mononuclear cells (PBMCs) were isolated from monkey blood and treated with ODNs SA-1-SA-10 (Table 7) and with eleven previously-tested unmodified ODNs derived from the HIV genome (S1, S4, S5, S9, S12, S13, S17, S18, S23, and S25). Production of cytokines IL-12, TNF-α, and IL-6 was measured by ELISA. The results are presented in FIG. 15. While PBMC production of TNF-α (FIG. 15B) was comparable for both sets of ODNs with unmodified HIV sequences, IL-12 production (FIG. 15A) and IL-6 production (FIG. 15C) were pronounced in cells treated with ODNs SA-1-SA-10.

In sum, these data demonstrate that HIV-derived ODNs can exert an immunostimulatory effect as determined by increase cytokine production in both human and monkey lymphocytes.

TABLE 7

Sequences of HIV-Derived CpG Oligonucleotides

| Name | Sequences | CG Cores |
|---|---|---|
| SA-1 | GCGCGCACGGCAAGAGGCGAGGGG (SEQ ID NO: 75) | 4 |
| SA-2 | CTCTCTCGACGCAGGACTCGGCTT (SEQ ID NO: 76) | 3 |
| SA-3 | ATCGATGGGAAAAAATTCGGTTAA (SEQ ID NO: 77) | 2 |
| SA-4 | AGAACGATTCGCAGTTAATCCTGG (SEQ ID NO: 78) | 2 |
| SA-5 | GATCCATTCGATTAGTGAACGGAT (SEQ ID NO: 79) | 1 |
| SA-6 | TTCACCATTATCGTTTCAGACCCA (SEQ ID NO: 80) | 1 |
| SA-7 | TAATAATAAGACGTTCAATGGAAC (SEQ ID NO: 81) | 1 |
| SA-8 | TTCGCCACATACCTAGAAGAATAA (SEQ ID NO: 82) | 1 |

TABLE 7-continued

Sequences of HIV-Derived CpG Oligonucleotides

| Name | Sequences | CG Cores |
|---|---|---|
| SA-9 | GGAGACAGCGACGAAGAGCTCATC (SEQ ID NO: 83) | 2 |
| SA-10 | GGGACCCGACAGGCCCGAAGGAAT (SEQ ID NO: 84) | 2 |

Example 9

Education of Human Lymphocytes

Figure 16:
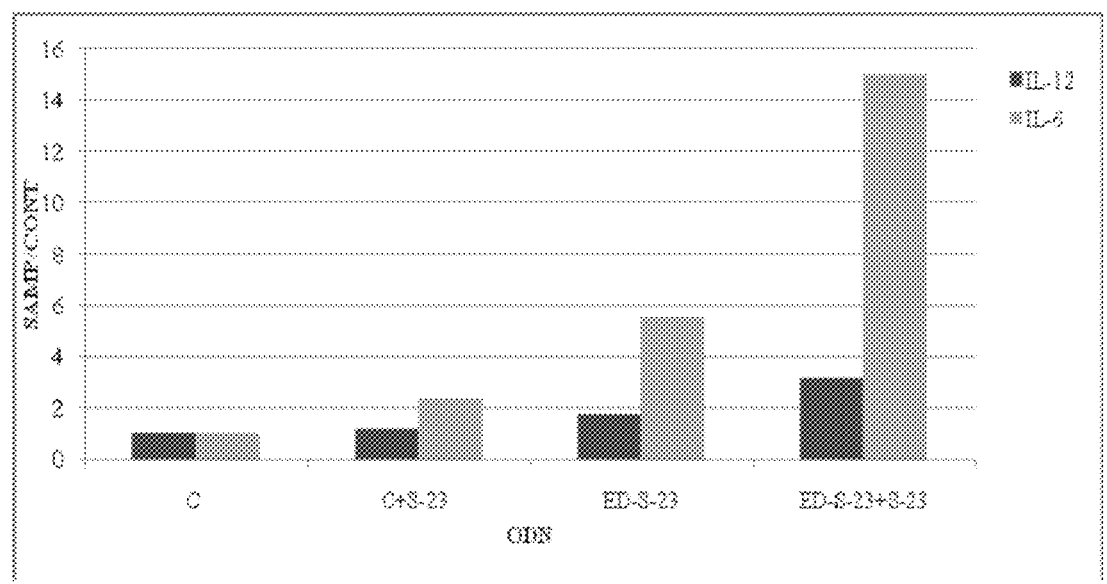
FIG. 16 is a bar graph depicting IL-12 and IL-6 cytokine production in human PBMCs 5 days after treatment with a HIV-derived ODN. C=control (naïve) human PBMCs. ED-S23="educated cells" human PBMCs. C+S23=naïve human PBMCs treated with the unmodified ODN. ED-S23+S23=educated human PBMCs subjected to a second treatment with unmodified ODN S23.

To test the effect of "priming" human lymphocytes with an immunostimulatory oligonucleotide, peripheral blood mononuclear cells were isolated from human blood and treated with unmodified ODN S23 derived from the HIV genome. After 5 days, educated cells were treated again with ODN S23. The production of IL-12 and IL-6 cytokines was measured by ELISA. The results are presented in FIG. 16. The PBMCs appeared to be primed to the entry of ODN S23 because IL-12 production was greatly enhanced in educated cells treated with S23 five days following the first treatment (FIG. 16). Production of cytokine IL-6 also was also increased in educated cells in five days after the first treatment.

Example 10

Education of Monkey Lymphocytes

Figure 17:
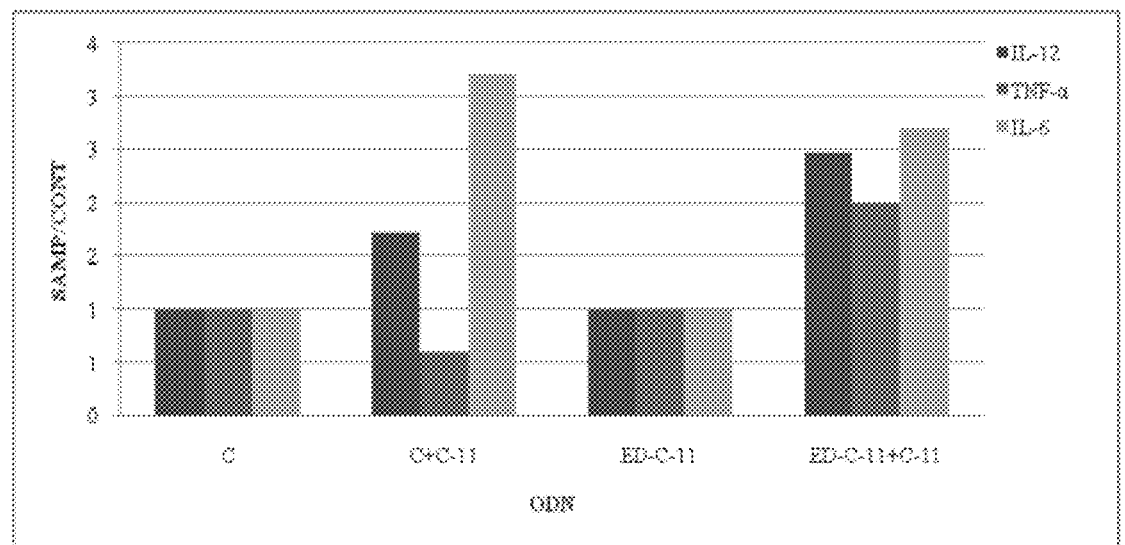
FIG. 17 is a bar graph depicting IL-12, TNF-α, and IL-6 cytokine production in monkey PBMCs 6 days after treatment with a SIV-derived ODN. C=control (untreated) monkey lymphocytes. C+C-11=control cells treated with ODN C-11. ED-C-11=educated cells with ODN C-11. ED-C11+C-11=educated cells treated with ODN C-11 six days after the first treatment.

To test the effect of "priming" monkey lymphocytes with an immunostimulatory oligonucleotide, peripheral blood mononuclear cells were isolated from monkey blood and treated with unmodified ODN C-11 derived from the SIV genome. Six days after an initial treatment, educated cells were treated again with ODN C-11. The production of IL-12, TNF-α, and IL-6 cytokines was measured by ELISA. The results are presented in FIG. 17. The monkey lymphocytes appeared to be primed to the entry of ODN C-11 because cytokine production was greatly enhanced in educated cells treated with C-11 six days following the first treatment (FIG. 17).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for stimulating lymphocyte cytokine production comprising contacting lymphocytes with an isolated nucleic acid consisting of from 20-84 contiguous nucleotides of a mammalian retroviral sequence, wherein said sequence comprises at least one CpG motif, with the proviso that at least one non-thymidine nucleotide 1, 2, or 3 bases immediately 5' or immediately 3' to said CpG motif is substituted with thymidine under conditions wherein said cytokine production is enhanced relative to uncontacted lymphocytes: wherein said nucleic acid consists of a sequence selected from the group consisting of SEQ ID NO: 30, 31, 34, 37, 40, 49, 51.

2. The method of claim 1, wherein said nucleic acid is 20-50 nucleotides in length.

3. The method of claim 1, wherein said nucleic acid is 24 nucleotides in length.

4. The method of claim 1, wherein said mammalian retroviral sequence is a HIV genomic sequence.

5. The method of claim 1, wherein said mammalian retroviral sequence is a SIV genomic sequence.

6. The method of claim 1, wherein said contacted lymphocytes form primed lymphocytes.

7. The method of claim 1, wherein said contacting further comprises application of a therapeutic antigen.

8. The method of claim 1, wherein said stimulation is measured according to a TLR-9 antagonism assay.

9. The method of claim 1, wherein said cytokine is selected from the group consisting of IL-6, IL-10, IL-12, and TNF-α, or any combination thereof.

* * * * *

SEQUENCE LISTING

<160> NUMBER OF SEQ ID NOS: 101

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 1
ttcactccca acgaagacaa gata                                            24

<210> SEQ ID NO 2
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 2
aatggatgac ccggagagag aagt                                            24

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 3
ggtttgacag ccgcctagca tttc                                            24

<210> SEQ ID NO 4
<211> LENGTH: 24
<212> TYPE: DNA

```
<213> ORGANISM: Artificial Sequence
<220> FEATURE:
<223> OTHER INFORMATION: Synthetic oligonucleotide

<400> SEQUENCE: 4
actgctgaca tcgagcttgc taca                                              24

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 5
aagggacttt ccgctgggga cttt                                              24

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 6
ctggggagtg gcgagccctc agat                                              24

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 7
tagtgtgtgc ccgtctgttg tgtg                                              24

<210> SEQ ID NO 8
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 8
tctagcagtg gcgcccgaac aggg                                              24

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 9
aggagctctc tcgacgcagg actc                                              24

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
acggcaagag gcgaggggcg gcga                                              24
```

<210> SEQ ID NO 11
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 11
actggtgagt acgccaaaaa tttt					24

<210> SEQ ID NO 12
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 12
gagaattaga tcgatgggaa aaaa					24

<210> SEQ ID NO 13
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 13
ctagaacgat tcgcagttaa tcct					24

<210> SEQ ID NO 14
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 14
ggtccaaaat gcgaacccag attg					24

<210> SEQ ID NO 15
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 15
ctctttggca acgacccctc gtca					24

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 16
ataccacatc ccgcagggtt aaaa					24

<210> SEQ ID NO 17
<211> LENGTH: 24
<212> TYPE: DNA
<213> ORGANISM: Artificial Sequence
<220> FEATURE:
<223> OTHER INFORMATION: Synthetic oligonucleotide

```
<400> SEQUENCE: 17
caccggtgct acggttaggg ccgc                                              24

<210> SEQ ID NO 18
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 18
gcctagtgtt acgaaactga caga                                              24

<210> SEQ ID NO 19
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 19
agtacatgta acgcaaccta tacc                                              24

<210> SEQ ID NO 20
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 20
aatagtagta gcgggagaat gata                                              24

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 21 gaaaagaat ccgtatccag agag                                               24

<210> SEQ ID NO 22
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 22
agaaattgta acgcacagtt ttaa                                              24

<210> SEQ ID NO 23
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 23
ttcaccatta tcgtttcaga ccca                                              24

<210> SEQ ID NO 24
<211> LENGTH: 24
<212> TYPE: DNA
```

<213> ORGANISM: Artificial Sequence
<220> FEATURE:
<223> OTHER INFORMATION: Synthetic oligonucleotide

<400> SEQUENCE: 24
cccgacaggc ccgaaggaat agaa                                              24

<210> SEQ ID NO 25
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 25
actgctgaca tcgagcttgc taca                                              24

<210> SEQ ID NO 26
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 26
tcgtcgtttt ttcgtttttt cgtt                                              24

<210> SEQ ID NO 27
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 27
tcgtcgtttt gtcgttttgt cgtt                                              24

<210> SEQ ID NO 28
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 28
ttcactccct tcgttgacaa gata                                              24

<210> SEQ ID NO 29
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 29
aatggatgat tcgttgagag aagt                                              24

<210> SEQ ID NO 30
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 30
ggtttgacat tcgtttagca tttc                                              24

```
<210> SEQ ID NO 31
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 31
actgctgact tcgttcttgc taca                                          24

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 32
aagggacttt tcgttgggga cttt                                          24

<210> SEQ ID NO 33
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 33
ctggggagtt tcgttccctc agat                                          24

<210> SEQ ID NO 34
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 34
tagtgtgtgt tcgtttgttg tgtg                                          24

<210> SEQ ID NO 35
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 35
tctagcagtt tcgttcgaac aggg                                          24

<210> SEQ ID NO 36
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 36
aggagctctt tcgtcgtagg attc                                          24

<210> SEQ ID NO 37
<211> LENGTH: 24
<212> TYPE: DNA
<213> ORGANISM: Artificial Sequence
<220> FEATURE:
<223> OTHER INFORMATION: Synthetic oligonucleotide
```

```
<400> SEQUENCE: 37
acgttaagat tcgttgttcg tcgt                                          24

<210> SEQ ID NO 38
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 38
tttggtgagt tcgttaaaaa tttt                                          24

<210> SEQ ID NO 39
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 39
gagaattaga tcgttgggaa aaaa                                          24

<210> SEQ ID NO 40
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 40
ctagttcgtt tcgttgttaa tcct                                          24

<210> SEQ ID NO 41
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 41
ggtccaaaat tcgttcccag attg                                          24

<210> SEQ ID NO 42
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 42
ctctttggct tcgttccttc gtta                                          24

<210> SEQ ID NO 43
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 43
ataccacatt tcgtagggtt aaaa                                          24

<210> SEQ ID NO 44
<211> LENGTH: 24
<212> TYPE: DNA
```

```
<213> ORGANISM: Artificial Sequence
<220> FEATURE:
<223> OTHER INFORMATION: Synthetic oligonucleotide

<400> SEQUENCE: 44
catcgttgct tcgtttaggt tcgt                                              24

<210> SEQ ID NO 45
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 45
gcctagtgtt tcgttactga caga                                              24

<210> SEQ ID NO 46
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 46
agtacatgtt tcgttaccta tacc                                              24

<210> SEQ ID NO 47
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 47
aatagtagtt tcgttagaat gata                                              24

<210> SEQ ID NO 48
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 48
gaaaaagaat tcgtttccag agag                                              24

<210> SEQ ID NO 49
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 49
agaaattgta tcgttcagtt ttaa                                              24

<210> SEQ ID NO 50
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 50
ttcaccatta tcgtttcaga ccca                                              24
```

```
<210> SEQ ID NO 51
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 51
ttcgttaggt tcgttggaat agaa                                          24

<210> SEQ ID NO 52
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 52
actgctgact tcgttcttgc taca                                          24

<210> SEQ ID NO 53
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 53
agggtgccat tcgtgctagg gttt                                          24

<210> SEQ ID NO 54
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 54
gcctgggtgt tcgctggtta gcct                                          24

<210> SEQ ID NO 55
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 55
acagaagctt tcgaggcttg ggat                                          24

<210> SEQ ID NO 56
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 56
ctcgacacgt tcgagaagat tagg                                          24

<210> SEQ ID NO 57
<211> LENGTH: 24
<212> TYPE: DNA
<213> ORGANISM: Artificial Sequence
<220> FEATURE:
<223> OTHER INFORMATION: Synthetic oligonucleotide
```

```
<400> SEQUENCE: 57
gtctccgcgc acgttaaatg cgtg                                          24

<210> SEQ ID NO 58
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 58
gcttaggagt gcgttatcat gtct                                          24

<210> SEQ ID NO 59
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 59
ataaacctgc tcgcttagtc gcta                                          24

<210> SEQ ID NO 60
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 60
ttgctgagcg tcggagaggg acga                                          24

<210> SEQ ID NO 61
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 61
cgcgacaggg gcgcgggtcc catt                                          24

<210> SEQ ID NO 62
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 62
aagcctcgac acgttcgaga agat                                          24

<210> SEQ ID NO 63
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 63
cccgttggaa ccgacaggct ccga                                          24

<210> SEQ ID NO 64
<211> LENGTH: 24
<212> TYPE: DNA
```

```
<213> ORGANISM: Artificial Sequence
<220> FEATURE:
<223> OTHER INFORMATION: Synthetic oligonucleotide

<400> SEQUENCE: 64
attgtccgat ccgcttatcg ggca                                              24

<210> SEQ ID NO 65
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 65
ctccagacgg ccgccgcctg caag                                              24

<210> SEQ ID NO 66
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 66
cccgaagttg gcggtggagt accg                                              24

<210> SEQ ID NO 67
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 67
cggtggagta ccgcccggac atgt                                              24

<210> SEQ ID NO 68
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 68
tggatcggag gcggtacagg ggcg                                              24

<210> SEQ ID NO 69
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 69
gctcgcttag tcgctatatt ggag                                              24

<210> SEQ ID NO 70
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 70
tcgctggctt gtaactcagt ctct                                              24
```

<210> SEQ ID NO 71
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 71
ccgagagtct ttggcttctg cttt                                            24

<210> SEQ ID NO 72
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 72
ccgctaaaat gctttaattg tggc                                            24

<210> SEQ ID NO 73
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 73
ccaatccgga ttgtaaattg attc                                            24

<210> SEQ ID NO 74
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 74
actgcaatgg gcgcagcggc aaca                                            24

<210> SEQ ID NO 75
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 75
gcgcgcacgg caagaggcga gggg                                            24

<210> SEQ ID NO 76
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 76
ctctctcgac gcaggactcg gctt                                            24

<210> SEQ ID NO 77
<211> LENGTH: 24
<212> TYPE: DNA
<213> ORGANISM: Artificial Sequence
<220> FEATURE:
<223> OTHER INFORMATION: Synthetic oligonucleotide

```
<400> SEQUENCE: 77
atcgatggga aaaaattcgg ttaa                                         24

<210> SEQ ID NO 78
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 78
agaacgattc gcagttaatc ctgg                                         24

<210> SEQ ID NO 79
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 79
gatccattcg attagtgaac ggat                                         24

<210> SEQ ID NO 80
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 80
ttcaccatta tcgtttcaga ccca                                         24

<210> SEQ ID NO 81
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 81
taataataag acgttcaatg gaac                                         24

<210> SEQ ID NO 82
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 82
ttcgccacat acctagaaga ataa                                         24

<210> SEQ ID NO 83
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 83
ggagacagcg acgaagagct catc                                         24

<210> SEQ ID NO 84
<211> LENGTH: 24
<212> TYPE: DNA
```

```
<213> ORGANISM: Artificial Sequence
<220> FEATURE:
<223> OTHER INFORMATION: Synthetic oligonucleotide

<400> SEQUENCE: 84
gggacccgac aggcccgaag gaat                                              24

<210> SEQ ID NO 85
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 85
ccgccgtttt gtcgttttgt cgtt                                              24

<210> SEQ ID NO 86
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 86
tcgtcgtttt gccgttttgc cgtt                                              24

<210> SEQ ID NO 87
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 87
tcgtcgtttt gtcgctttgt cgct                                              24

<210> SEQ ID NO 88
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 88
tcgtcgtttt gacgttttga cgtt                                              24

<210> SEQ ID NO 89
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 89
tcgtcgtttt gtcgatttgt cgat                                              24

<210> SEQ ID NO 90
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 90
tcgtcgtttt aacgttttaa cgtt                                              24
```

<210> SEQ ID NO 91
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 91
tcgtcgtttt gtcgaattgt cgaa                                           24

<210> SEQ ID NO 92
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 92
ttattgtttt attatttcca aatt                                           24

<210> SEQ ID NO 93
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 93
tgcttaaaga ttattgtttt attatttcca aattgttctc ttaa                     44

<210> SEQ ID NO 94
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 94
tcctgaggat tgcttaaaga ttattgtttt attatttcca aattgttctc ttaatttgct    60
agct                                                                 64

<210> SEQ ID NO 95
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 95
ctgggtcccc tcctgaggat tgcttaaaga ttattgtttt attatttcca aattgttctc    60
ttaatttgct agctatct                                                  78

<210> SEQ ID NO 96
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 96
tcgtcgtttt atcgtttcca cgtt                                           24

<210> SEQ ID NO 97
<211> LENGTH: 44
<212> TYPE: DNA

```
<213> ORGANISM: Artificial Sequence
<220> FEATURE:
<223> OTHER INFORMATION: Synthetic oligonucleotide

<400> SEQUENCE: 97
tgcttaaaga tcgtcgtttt atcgtttcca cgttgttctc ttaa                44

<210> SEQ ID NO 98
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 98
tcctgaggat tgcttaaaga tcgtcgtttt atcgtttcca cgttgttctc ttaatttgct    60
agct                                                                64

<210> SEQ ID NO 99
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 99
ctgggtcccc tcctgaggat tgcttaaaga tcgtcgtttt atcgtttcca cgttgttctc    60
ttaatttgct agctatct                                                 78

<210> SEQ ID NO 100
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 100
tcgtcgaacg ttcgagatga t                                             21

<210> SEQ ID NO 101
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 101
tcgtgcaagc ttgcagatga t                                             21
```